(12) United States Patent
Kohn et al.

(10) Patent No.: US 10,202,490 B2
(45) Date of Patent: Feb. 12, 2019

(54) BIOCOMPATIBLE POLYMERS FOR MEDICAL DEVICES

(71) Applicant: Rutgers, The State University of New Jersey, New Brunswick, NJ (US)

(72) Inventors: Joachim B. Kohn, Piscataway, NJ (US); Durgadas Bolikal, Edison, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 15/440,249

(22) Filed: Feb. 23, 2017

(65) Prior Publication Data

US 2017/0158819 A1    Jun. 8, 2017

Related U.S. Application Data

(62) Division of application No. 13/501,255, filed as application No. PCT/US2010/052208 on Oct. 11, 2010, now Pat. No. 9,605,112.

(60) Provisional application No. 61/250,550, filed on Oct. 11, 2009.

(51) Int. Cl.
| | |
|---|---|
| C08G 69/44 | (2006.01) |
| A61L 24/04 | (2006.01) |
| A61L 27/18 | (2006.01) |
| A61L 31/06 | (2006.01) |
| C08G 69/08 | (2006.01) |

(52) U.S. Cl.
CPC ............ *C08G 69/44* (2013.01); *A61L 24/046* (2013.01); *A61L 27/18* (2013.01); *A61L 31/06* (2013.01); *C08G 69/08* (2013.01)

(58) Field of Classification Search
CPC combination set(s) only.
See application file for complete search history.

(56) References Cited

U.S. PATENT DOCUMENTS

| | | |
|---|---|---|
| 3,636,956 A | 1/1972 | Schneider |
| 3,663,515 A | 5/1972 | Hostettler et al. |
| 4,043,981 A | 8/1977 | O'Brien |
| 4,162,314 A | 7/1979 | Gottschlich et al. |
| 4,230,817 A | 10/1980 | Charbonneau |
| 4,331,782 A | 5/1982 | Linden |
| 4,476,294 A | 10/1984 | Mark |
| 4,744,365 A | 5/1988 | Kaplan et al. |
| 4,747,956 A | 5/1988 | Kiniwa |
| 4,822,829 A | 4/1989 | Muller et al. |
| 4,980,449 A | 12/1990 | Kohn et al. |
| 5,003,004 A | 3/1991 | Simms |
| 5,066,772 A | 11/1991 | Tang et al. |
| 5,082,925 A | 1/1992 | Shalaby et al. |
| 5,099,060 A | 3/1992 | Kohn et al. |
| 5,216,115 A | 6/1993 | Kohn et al. |
| 5,219,564 A | 6/1993 | Zalipsky et al. |
| 5,403,347 A | 4/1995 | Roby et al. |
| 5,431,679 A | 7/1995 | Bennett et al. |
| 5,587,507 A | 12/1996 | Kohn et al. |
| 5,660,822 A | 8/1997 | Poiani et al. |
| 5,665,831 A | 9/1997 | Neuenschwander et al. |
| 5,670,602 A | 9/1997 | Kohn et al. |
| 5,698,661 A | 12/1997 | Ferruti et al. |
| 5,702,717 A | 12/1997 | Cha et al. |
| 5,854,383 A | 12/1998 | Emeta et al. |
| 5,916,998 A | 6/1999 | Ferruti et al. |
| 5,952,450 A | 9/1999 | Ishihara et al. |
| 6,120,491 A | 9/2000 | Kohn et al. |
| 6,150,491 A | 11/2000 | Akkara |
| 6,228,969 B1 | 5/2001 | Lee et al. |
| 6,316,585 B1 | 11/2001 | Lele et al. |
| 6,355,754 B1 | 3/2002 | Olson et al. |
| 6,475,477 B1 | 11/2002 | Kohn et al. |
| 6,592,899 B2 | 7/2003 | Fowers et al. |
| 6,602,497 B1 | 8/2003 | Kohn et al. |
| 6,943,214 B2 | 9/2005 | Flexman |
| 7,166,134 B2 | 1/2007 | Datta et al. |
| 7,169,187 B2 | 1/2007 | Datta et al. |
| 7,479,157 B2 | 1/2009 | Weber et al. |
| 8,252,877 B2 | 8/2012 | Hirano et al. |
| 8,252,887 B2 | 8/2012 | Bolikal et al. |
| 8,476,399 B2 | 7/2013 | Bolikal et al. |
| 8,551,511 B2 | 10/2013 | Brandom et al. |
| 2001/0046505 A1 | 11/2001 | Kohn et al. |
| 2003/0068384 A1 | 4/2003 | Brocchini et al. |

(Continued)

FOREIGN PATENT DOCUMENTS

| | | |
|---|---|---|
| CA | 2412161 A1 | 12/2001 |
| CA | 2412718 A1 | 1/2002 |

(Continued)

OTHER PUBLICATIONS

Shiotani et al. (Chem. Pharm. Bull. 16(2), published 1968, pp. 239-245).*
Liskamp (Journal of Organic Chemistry, pp. 1817-1824, published 2006).*
Berse et al. (Journal of Organic Chemistry, vol. 27, pp. 3489-3495, Published 1962).*
Milewska (Amino Acids, published 1994, pp. 89-96).*
Caracciolo et al., "Effect of the hard segment chemistry and structure on the thermal and mechanical properties of novel biomedical segmented poly(esterurethanes)", J. Mater Sci: Mater Med vol. 20, pp. 145-155 (2009).
Kaneko et al., "Environmentally degradable, high-performance thermoplastics from phenolic phytomonomers", Nature Materials, vol. 5, pp. 966-970 (2006).

(Continued)

*Primary Examiner* — Alma Pipic
(74) *Attorney, Agent, or Firm* — Fox Rothschild LLP

(57) ABSTRACT

The present invention relates to new classes of monomeric compounds, which may be polymerized to form novel biodegradable and bioresorble polymers and copolymers. These polymers and co-polymers, while not limited thereto, may be adapted for radio-opacity and are useful for medical device applications and controlled release therapeutic formulations.

19 Claims, No Drawings

(56) References Cited

U.S. PATENT DOCUMENTS

| | | |
|---|---|---|
| 2004/0082734 A1 | 4/2004 | Hatton et al. |
| 2005/0106119 A1 | 5/2005 | Brandom et al. |
| 2006/0024266 A1 | 2/2006 | Brandom et al. |
| 2006/0034769 A1 | 2/2006 | Kohn et al. |
| 2006/0034891 A1 | 2/2006 | Lawin et al. |
| 2006/0036316 A1 | 2/2006 | Zeltinger et al. |
| 2006/0178477 A1 | 8/2006 | Neuenschwander |
| 2007/0117959 A1 | 5/2007 | Shastri et al. |
| 2007/0135355 A1 | 6/2007 | Bezwada |
| 2007/0183996 A1 | 8/2007 | Okombi et al. |
| 2007/0190151 A1 | 8/2007 | Chai et al. |
| 2007/0231365 A1 | 10/2007 | Wang et al. |
| 2007/0282435 A1 | 12/2007 | Wang et al. |
| 2008/0063685 A1 | 3/2008 | Wang et al. |
| 2008/0112999 A1 | 5/2008 | Baluca |
| 2008/0146504 A1 | 6/2008 | Bonnin |
| 2008/0152690 A1 | 6/2008 | Kohn et al. |
| 2008/0187567 A1 | 8/2008 | Kohn et al. |
| 2008/0221295 A1 | 9/2008 | Ishikawa et al. |
| 2008/0243049 A1 | 10/2008 | Hardy |
| 2008/0243228 A1 | 10/2008 | Wang et al. |
| 2008/0269874 A1 | 10/2008 | Wang et al. |
| 2009/0004243 A1 | 1/2009 | Pacetti et al. |
| 2009/0035350 A1 | 2/2009 | Stankus et al. |
| 2009/0088835 A1 | 4/2009 | Wang |
| 2010/0234555 A1 | 9/2010 | Bolikal et al. |
| 2013/0203713 A1 | 8/2013 | Kohn et al. |
| 2015/0045451 A1 | 2/2015 | Bolikal et al. |

FOREIGN PATENT DOCUMENTS

| | | |
|---|---|---|
| DE | 3523977 A1 | 1/1986 |
| JP | H0618946 A | 1/1994 |
| JP | H07292084 A | 11/1995 |
| JP | H07295221 A | 11/1995 |
| JP | H11513985 A | 11/1999 |
| JP | 2004-513971 | 5/2004 |
| JP | 2007-506791 | 3/2007 |
| JP | 2007131622 A | 5/2007 |
| JP | 2008506019 A | 2/2008 |
| JP | 2008-509722 | 4/2008 |
| JP | 2008-510034 | 4/2008 |
| JP | 2009503187 A | 1/2009 |
| WO | 1989/001005 A1 | 2/1989 |
| WO | 91/06569 A1 | 5/1991 |
| WO | 9715287 A1 | 5/1997 |
| WO | 1997/019996 | 6/1997 |
| WO | 1998/036013 A1 | 8/1998 |
| WO | 1999/024391 | 5/1999 |
| WO | 2005/030268 A1 | 4/2005 |
| WO | 2006/022754 A2 | 3/2006 |
| WO | 2006/060235 A2 | 6/2006 |
| WO | 2007/018544 A2 | 2/2007 |
| WO | 2007047244 A2 | 4/2007 |
| WO | 2007/050583 A2 | 5/2007 |
| WO | 2007/056134 | 5/2007 |
| WO | 2007/143698 | 12/2007 |
| WO | 2008/082738 A2 | 7/2008 |
| WO | 2008105652 A1 | 9/2008 |
| WO | 2010/033640 | 3/2010 |
| WO | 2010/042917 | 4/2010 |
| WO | 2010042917 A1 | 4/2010 |
| WO | 2010042918 A1 | 4/2010 |
| WO | 2015/126666 A1 | 8/2015 |

OTHER PUBLICATIONS

Kaneko, "High-Performance Functional Ecopolymers Based on Flora and Fauna", Chemical Record vol. 7(4), pp. 210-219 (2007).
Mosher et al., "Polypeptides from r-Phenylalanine Mustard", J. Med. Chem. vol. 7(5), pp. 650-652 (1964).
Schmaljohann et al., Conversion dependence of the structural units and the degree of branching of a hyperbranched polyester based on 4,4-bis-(4'-hydroxyphenyl)pentanoic acid determined by NMR spectroscopy, Acta Polym. vol. 50, pp. 196-204 (1999).
Mikroyannidis, "Synthesis, properties and crosslinking of unsaturated cyano-substituted homo- and copolyesters prepared from 1-hydroxy-4-(2-cyano-2-carboxyvinyl)benzene", Polymer vol. 36(6), pp. 1287-1293 (1995).
Fuso et al., "Poly[(w-hydroxyalkyl)thio-a-cyanocinnamates]. Linear Polyesters with NLO-Phores in the Main Chain", Macromolecules vol. 24, pp. 1710-1713 (1991).
Sousa, A., et al., "Selective Protein Adsorption on a Phase-Separated Solvent-Cast Polymer Blend", Langmuir, 22, 2006, pp. 6286-6292.
Tangpasuthadol, V., et al., "Thermal properties and physical ageing behaviour of tyrosine-derived polycarbonates", Biomaterials, 1996, vol. 17, No. 4., pp. 463-468.
Sarkar, D., et al., Structure-Property Relationship of L-Tyrosine-Based Polyurethanes for Biomaterial Applications, Journal of Applied Polymer Science, vol. 108, 23435-2355 (2008).
Polycarprolactone diol, 2011 obtained from the Sigma-Aldrich website: (http://www.sigmaaldrich.com/catalog/ProductDetail.do?D7=0&N5=SEARCH_CONCAT_PNO%7CBRAND_KEY&N4=189421%7CALDRICH&N25=0&QS=ON&F=SPEC).
Teng et al., "Synthesis and characterization of poly(L-lactic acid)-poly(e- caprolactone) multiblock copolymers by melt polycondensation," Journal of Polymer Science Part A: Polymer Chemistry. 42: pp. 5045-5053, 2004. (Abstract).
Mligiliche et al., ,"Poly lactic acid-caprolactone copolymer tube with a denatured skeletal muscle segment inside as a guide for peripheral nerve regeneration: A morphological and electrophysiological evaluation of the regenerated nerves," Anatomical Science International, vol. 78, No. 3, Sep. 2003, pp. 156-161. (Abstract).
Nathan et al., Bio. Cong. Chem., 4, 54-62 (1993).
Nathan, Macromol., 25, 4476 (1992).
Dobrzynski et al. Structure-Property Relationships of Copolymers Obtained by Ring-Opening Polymerization of Glycolide and e-Caprolactone. Part 1. Synthesis and Characterization. Biomacromolecules 6(1): 483-488. 2005.
Latham, K. et al., "Development of Support Matrices for Affinity Chromatography of Thyroid Hormone Receptors," The J. of Biological Chem, Dec. 10, 1981, vol. 256, pp. 12088-12093.
Perez, P. et al., "Bioresorbable and Nonresorbable Macroporous Thermosensitive Hydrogels Prepared by Cryopolymerization. Role of the Cross-Linking Agent," Biomacromolecules 2008, vol. 9, pp. 66-74.
Tang, S. et al., "Synthesis and Characterization of Water-Soluble and Photostable L-DOPA Dendrimers," Organic Letters, 2006, vol. 8, No. 20, pp. 4421-4424.
Ross, et al.: "Carbon Suboxide and Proteins, III. The Reaction of Carbon Suboxide with Amino Acids"; Journal of Biological Chemistry, 1941, vol. 37, pp. 105-111.
Zhang et al.: "Synthesis and Biological Activities of QuinazolineDerivatives with Ortho-Phenol_Quaternary Ammonium Salt Groups", Bioorganic & Medicinal Chemistry, 2007, vol. 15, Issue 22, pp. 6920-6926.
Ross, et al.: "Carbon Suboxide and Proteins"; Journal of Biological Chemistry, Published 1941, vol. 37, pp. 105-111.
Imasaka et al: "New Biodegradable Polymers of L-lactic Acid and Aromatic Hydroxy Acids and Their Applications in Drug Delivery Systems", International Journal of Pharmaceutics, 1992, vol. 81, pp. 31-38.
Jin, et al: "Synthesis, Characterization, and in Vitro Degradation of a Novel Thermotropic Ternary Copolyester Based on p-Hydroxybenzoic Acid, Glycolic Acid, and p-Hydroxycinnamic Acid", Macromolecules, Jul. 3, 1995, vol. 28, No. 14, pp. 4785-4794.
Nagata, et al: "Biodegradable Elastic Photocured Polyesters Based on Adipic Acid, 4-hydroxycinnamic Acid and Poly (e-caprolactone) diols", Polymer, 2004, vol. 45, pp. 87-93.
Du, et al: "Synthesis, Characterization and Biodegradation of Biodegradable-cum-photoactive Liquid-Crystalline Copolyesters Derived From Ferulic Acid", Polymer, 2007, vol. 48, pp. 5541-5547.
Beaulieu, et al: "Non-Nucleoside Inhibitors of the Hepatitis C Virus NS5B Polymerase: Discovery of Benzimidazole 5-Carboxylic Amid Derivatives with Low-Nanomolar Potency", Bioorganic & Medicinal Chemistry Letters, 2004, vol. 14, pp. 967-971.

(56) References Cited

OTHER PUBLICATIONS

Cascales, et al: "Tiratricol Neutralizes Bacterial Endotoxins and Reduces Lipopolysaccharide-Induced TNF-x Production in the Cell", Chem Biol Drug Des, 2008, vol. 72, pp. 320-328.
Majeska, et al: "Effects of Plate Preparation on Results in Microbial Mutation Assays", Environmental and Molecular Mutagenesis, 1992, vol. 19, pp. 244-252.
Green et al., "Protective Groups in Organic Synthesis" 3rd Ed. John Wiley & Sons, New York, NY, 1999 (Abstract only).
Laurencin et al., "Poly(anhydride) administration in high doses in vivo: studies of biocompatibility and toxicology", J. Biomed. Mat. Res., Nov. 24, 1990, pp. 1463-1481 (Abstract only).
Matsusaki, M. et al., "Synthesis and Characterization of Novel Biodegradeable Polymers Composed of Hydroxycinnamic Acid and D,L-Lactic Acid", Journal of Applied Polymer Science, vol. 82, No. 10, Sep. 19, 2001, pp. 2357-2364.
Plate et al., "Comb-like Polymers. Structure and Properties." J. Polymer Sci., Macromolecular Reviews, Jan. 1974, vol. 8, No. 1, pp. 117-253 (Abstract only).
Wermann, et al., Photoreactive Polyanhydries Containing Cinnamic Acid Units in the Main Chain, Macromolecular Reports, A31 (Suppls. 6&7, 1279-1283 (1994).
XP-002762099, Database WPI, Week 199602, Thomson Scientific, 1996 (2 pages).
XP-002762086, Database Caplus, Chemical Abstracts Service, Feb. 1, 1995 (3 pages).
Imasaka, et al: "Synthesis and in Vitro Degradations of Low-Molecular-Weight Copolyesters Composed of L-lactic Acid and Aromatic Hydroxy Acids", Makromolekular Chemmie, 1990, vol. 191, pp. 2077-2082.
Plage et al: "Therman Degradation and Mass Spectrometric Fragmention Processes of Polyesters Studies by Time-/Temperature-Resolved Pyrolysis-Field Ionization Mass Spectrometry", Macromolecules, 1990, vol. 23, pp. 2642-2648.
5-(4-Carboxy-1,4-Dioxobutoxy)Tryptophan, Compound w2ith 5-Hydroxy-6-Methylpyridine-3,4-Dimethanol (1:1), Chemical Book, Retrieved from the Internet<URL: http://www.chemicalbook.com/ChemicalProductProperty_CN_CB1896543.htm>, Sep. 15, 2016.
Trisuwan et al., "Anthraquinone Cyclopentanone, and Napthoquinone Derivatives from the Sea Fan-Derived Fungi *Fusarium* spp. PSU-F14 and PSU-F135", Journal of Natural Products, vol. 73, No. 9, Sep. 24, 2010, pp. 1507-1511.
Trisuwan et al., "Supporting Information—Anthraquinone Cyclopentanone, and Napthoquinone Derivatives from the Sea Fan-Derived Fungi *Fusarium* spp. PSU-F14 and PSU-F135", Journal of Natural Products, Sep. 24, 2010, pp. 1-12.
Yang et al., "Phenolic Constituents from the Rhizomes of Gastrodia Elata", Database CA (online) Chemical Abstracts Service, Columbus, OH; Yang et al., "Phenolic constituents from the rhizomes of Gastrodia elata" XP002711180, retrieved frm STN Database accession No. 2007:23882 (abstract); Yang et al., "Phenolic constituents from the rhizomes of Gastrodia elata", Natural Product Research, 21(2) pp. 180-186 (abstract).
Krawczyk, et al: "A Study on Horseradish Peroxidase-Mediated Coupling of Phenolesters, Directed to Synthesis of Lythraceae Alkaloids", Bulletin of the Polish Academy of Sciences, 1986, vol. 34, No. 3-4, pp. 115-122.
Covello, et al: "Synthesis and Properties of 2-Hydroxy-And 2-Acetoxy-5-Iodobenzoic Acid Polyesters of Short-Chain Aliphatic Polyalcohols", Oct. 1, 1968, La Ricerca Scientifica, vol. 38, No. 10, pp. 933-936.

\* cited by examiner

BIOCOMPATIBLE POLYMERS FOR MEDICAL DEVICES

CROSS-REFERENCE TO RELATED APPLICATION

The present application claims priority benefit under 35 U.S.C. § 119(e) and the Paris Convention to U.S. Patent Application Ser. No. 61/250,550 filed Oct. 11, 2009, the disclosure of which is incorporated by reference in its entirety for all purposes.

This application is also related to U.S. patent application Ser. Nos. 12/577,203 and 12/577,205; and U.S. Provisional Patent Application Ser. No. 61/250,548, all of which were also filed on Oct. 11, 2009. The disclosures of all three applications are hereby incorporated by reference in their entirety for all purposes.

FIELD OF THE INVENTION

The present invention relates to new classes of monomeric compounds, which may be polymerized to form novel biodegradable and bioresorble polymers and co-polymers. These polymers and co-polymers, while not limited thereto, may be adapted for radio-opacity and are useful for medical device applications and controlled release therapeutic formulations.

The present invention thus also relates to new biocompatible polymers suitable for use in implantable medical devices and monomers for such polymers. In particular, the present invention relates to polymers polymerized from monomer analogs of compounds that naturally occur in the human body and that contribute advantageous synthesis, processing and material properties to the polymers prepared therefrom.

BACKGROUND OF THE INVENTION

Diphenols are monomeric starting materials for polycarbonates, polyiminocarbonates, polyarylates, polyurethanes and the like. Commonly owned U.S. Pat. No. 5,099,060 discloses diphenolic monomers based on 3-(4-hydroxyphenyl) propionic acid and L-tyrosine alkyl esters (desaminotyrosyl-tyrosine alkyl esters). Subsequent related patents involve variations of this basic monomer structure, including halogenated radiopaque diphenolic monomers, such as the 3,5-di-iododesaminotyrosyl-tyrosine esters (I2DTX, wherein X=ester group, e.g., E=ethyl, H=hexyl, O=octyl, etc.) disclosed by U.S. Patent Application Publication No. 2006/0034769. The disclosures of both publications are incorporated by reference. Examples of other polymers suitable for various bioengineering applications include those described in U.S. Pat. Nos. 5,665,831; 5,916,998 and 6,475,477, along with the polymers described in U.S. Patent Publication No. 2006/0024266, the disclosures of all of which are also incorporated by reference.

Although these monomers are useful in the synthesis of polymers for many medical implant applications, the rapidly evolving field of bioengineering has created a demand for a diverse library of different types of polymers offering a wide variety of choice of physical and mechanical properties. It is desirable that libraries of many different materials be available so that the specific polymer properties can be optimally matched with the requirements of the specific applications under development.

SUMMARY OF THE INVENTION

As set forth herein, the embodiments disclosed address these needs. Various embodiments provide polymer compositions derived from new monomers, medical devices containing such compositions, and methods of using such polymer compositions and devices.

New classes of monomeric compounds are provided, which may be polymerized to form novel polymers and co-polymers that, while not limited thereto, may be adapted for radio-opacity and are useful for medical device applications and controlled release therapeutic formulations, although not limited thereto. More specifically, the present invention introduces a novel class of monomers, which are polymerized to form polymers and copolymers with at least one or more aromatic repeating units that are analogs of tyrosine, thyronine, tryptophan and other compounds that naturally occur in the human body.

In one embodiment, monomer compounds are provided having the structure of formula Ia:

$$R_5—X_1—R—NR_3—X_7—B—X_8—[NR_3—R—X_6—]_fR_6 \quad \text{(Ia)}$$

wherein f is 0 or 1, $X_1$ and $X_6$ are independently selected from O, S and $NR_3$, wherein $R_3$ is selected from hydrogen and an alkyl group containing from one to six carbon atoms. $X_7$ and $X_8$ are independently selected from —(C=O)—$NR_3$— (urea), —(C=O)— (amide), —(C=O)—O— (carbamate) and —(C=O)—S— (thiocarbamate). Each R is independently selected from optionally substituted aromatic, heteroaromatic, aryl ether, haloaromatic alkyl, heteroalkyl, alkenyl and heteroalkenyl groups, each containing from one to ten carbon atoms, wherein at least one R has a pendant carboxylic acid or carboxylate group, or the thio or amide analog thereof. The number of carbon atoms in the pendant group is in addition to the number of carbon atoms of the R group. $R_5$ and $R_6$ are independently selected from hydrogen and an alkyl group containing from one to six carbon atoms.

B is selected from an optionally substituted alkyl group, an optionally substituted heteroalkyl group, an optionally substituted alkenyl group and an optionally substituted heteroalkenyl group, or B is selected so that HO—B—OH is a hydroxyl endcapped macromer, $H_2N$—B—$NH_2$ is an amino endcapped macromer and HS—B—SH is a thiol endcapped macromer.

R, $R_5$, $X_1$, $X_6$ and $R_6$ are selected so that at least one of $R_5$—$X_1$—R—$NH_2$ and $NH_2$—R—$X_6$—$R_6$ is an amino acid or a thio, amide or ester analog. In one embodiment R, $R_5$, $X_1$, $X_6$ and $R_6$ are selected so that both of $R_5$—$X_1$—R—$NH_2$ and $NH_2$—R—$X_6$—$R_6$ are amino acids. In an embodiment, R, $R_5$, $X_1$, $X_6$ and $R_6$ are selected so that both of $R_5$—$X_1$—R—$NH_2$ and $NH_2$—R—$X_6$—$R_6$ are alpha-amino acids. In another embodiment, R, $R_5$, $X_1$, $X_6$ and $R_6$ are selected so that both of $R_5$—$X_1$—R—$NH_2$ and $NH_2$—R—$X_6$—$R_6$ are naturally-occurring alpha-amino acids, i.e., amino acids that naturally occur in the human body. Amino acids that are not naturally-occurring include naturally-occurring amino acids to which substituent groups have been added to provide reactive polymerization groups.

In one embodiment at least one R is —$R_1$—Ar— or —Ar—$R_1$—, and Ar, $R_1$, $R_5$, $X_1$, $X_6$ and $R_6$ are selected so that at least one of $R_5$—$X_1$—R—$NH_2$ and $NH_2$—R—$X_6$—$R_6$ is:

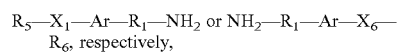

wherein Ar is independently a phenyl ring,

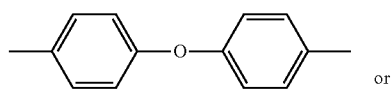

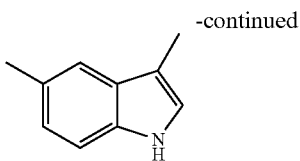

optionally substituted with from one to four substituents per aromatic ring independently selected from halogen, halomethyl, halo-methoxy, methyl, methoxy, thiomethyl, nitro, sulfoxide, and sulfonyl. At least one occurrence of $R_1$ has a pendant carboxylic acid or carboxylate group, or the thio or amide analog thereof, and each occurrence of $R_1$ is independently selected from optionally substituted aromatic, heteroaromatic, aryl ether, haloaromatic alkyl, heteroalkyl, alkenyl and heteroalkenyl groups each containing from one to ten carbon atoms.

In one embodiment, aromatic monomer compounds are provided having the structure of formula Ia':

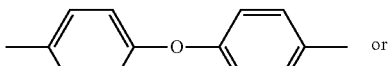   (Ia')

wherein f is 0 or 1, $X_1$ and $X_6$ are independently selected from O, S and $NR_3$ wherein $R_3$ is selected from hydrogen and an alkyl group containing from one to six carbon atoms. $X_7$ and $X_8$ are independently selected so that together with $NR_3$ an amide or urethane linkage is provided or the thio-analog thereof. $Ar_1$ and $Ar_2$ are each independently a phenyl ring,

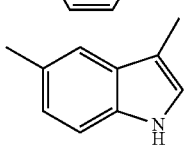

optionally substituted with from one to four substituents independently selected from halogen, halomethyl, halomethoxy, methyl, methoxy, thiomethyl, nitro, sulfoxide, and sulfonyl. $R_1$ and $R_2$ each comprise a pendant carboxylic acid or carboxylate group, or the thio or amide analog thereof, and are each independently selected from optionally substituted alkyl, heteroalkyl, alkenyl and heteroalkenyl groups each containing from one to ten carbon atoms. $R_5$ and $R_6$ are independently selected from hydrogen and an alkyl group containing from one to six carbon atoms. B is selected from an optionally substituted alkyl group, an optionally substituted heteroalkyl group, an optionally substituted alkenyl group and an optionally substituted heteroalkenyl group, or B, $X_7$ and $X_8$ are selected so that $HX_7$—B—$X_8H$ defines an endcapped elastomer.

The compounds of Formula Ia are prepared by reacting one mole of a compound having the structure $HX_3$—B—$X_4H$ with phosgene or triphosgene and either about one mole of the compound of Formula Ib (f=0) or about two moles of the compound of Formula Ib (f=1), wherein $X_3$ and $X_4$ are independently selected from O, S and $NR_3$, and Formula Ib has the structure:

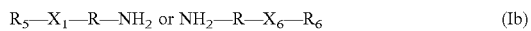   (Ib)

wherein R, $R_5$, $R_6$, $X_1$ and $X_6$ are the same as described above with respect to Formula Ia.

In another embodiment, aromatic monomer compounds are provided having the structure of formula IIa:

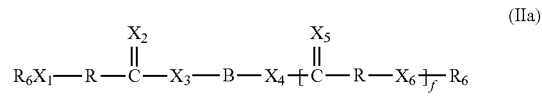   (IIa)

Wherein f is 0 or 1, $X_1$, $X_2$, $X_3$, $X_4$, $X_5$ and $X_6$ are independently selected from O, S and $NR_3$ wherein $R_3$ is selected from hydrogen and an alkyl group containing from one to six carbon atoms.

Each R is independently selected from optionally substituted aromatic, heteroaromatic, aryl ether, haloaromatic alkyl, heteroalkyl, alkenyl and heteroalkenyl groups, each containing from one to ten carbon atoms, wherein at least one R has a pendant amino group or backbone imine. The number of carbon atoms in the pendant group is in addition to the number of carbon atoms of the R group. $R_5$ and $R_6$ are independently selected from hydrogen and an alkyl group containing from one to six carbon atoms.

B is selected from an optionally substituted alkyl group, an optionally substituted heteroalkyl group, an optionally substituted alkenyl group and an optionally substituted heteroalkenyl group, or B, $X_3$ and $X_4$ are selected so that $HX_3$—B—$X_4H$ defines a hydroxyl endcapped macromer, a mercapto endcapped macromer or an amine endcapped macromer.

R, $R_5$, $X_1$, $X_2$, $X_5$, $X_6$ and $R_6$ are selected so at least one of $R_5$—$X_1$—R—(C=$X_2$)OH and HO—(C=$X_5$)—R—$X_6$—$R_6$ is an amino or imino acid. In one embodiment R, $R_5$, $X_1$, $X_2$, $X_5$, $X_6$ and $R_6$ are selected so that both of $R_5$—$X_1$—R—(C=$X_2$)OH and HO—(C=$X_5$)—R—$X_6$—$R_6$ are amino acids. In another embodiment, R, $R_5$, $X_1$, $X_2$, $X_5$, $X_6$ and $R_6$ are selected so both of $R_5$—$X_1$—R—(C=$X_2$)OH and HO—(C=$X_5$)—R—$X_6$—$R_6$ are alpha-amino acids. In another embodiment, R, $R_5$, $X_1$, $X_2$, $X_5$, $X_6$ and $R_6$ are selected so both of $R_5$—$X_1$—R—(C=$X_2$)OH and HO—(C=$X_5$)—R—$X_6$—$R_6$ are naturally-occurring alpha-amino acids, i.e., amino acids that naturally occur in the human body. Amino acids that are not naturally-occurring include naturally-occurring amino acids to which substituent groups have been added to provide reactive polymerization groups.

In an embodiment at least one R is —$R_1$—Ar— or —Ar—$R_1$—, and Ar, $R_1$, $R_5$, $X_1$, $X_2$, $X_5$, $X_6$ and $R_6$ are selected so at least one of $R_5$—$X_1$—R—(C=$X_2$)OH and HO—(C=$X_5$)—R—$X_6$—$R_6$ is $R_5$—$X_1$—Ar—R—(C=$X_2$)OH or HO—(C=$X_5$)—$R_1$—Ar—$X_6$—$R_6$, respectively, wherein Ar is independently a phenyl ring,

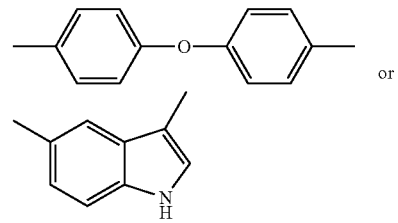

optionally substituted with from one to four substituents per aromatic ring independently selected from halogen, halomethyl, halomethoxy, methyl, methoxy, thiomethyl, nitro, sulfoxide, and sulfonyl. At least one occurrence of $R_1$ has an optionally-substituted pendant amino group or backbone imine, and each occurrence of $R_1$ is independently selected from optionally substituted aromatic, heteroaromatic, aryl ether, haloaromatic alkyl, heteroalkyl, alkenyl and heteroalkenyl groups each containing from one to ten carbon atoms. $R_5$ and $R_6$ are independently selected from hydrogen and an alkyl group containing from one to six carbon atoms.

The compounds of Formula IIa are prepared by reacting one mole of a compound having the structure $HX_3$—B—$X_4H$ with either about one mole of the compound of Formula IIb (f=0) or about two moles of the compound of Formula IIb (f=1), and Formula IIb has the structure:

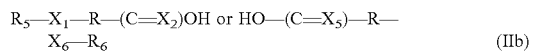

(IIb)

wherein R, $R_5$, $R_6$, $X_1$, $X_2$, $X_5$ and $X_6$ are the same as described above with respect to Formula IIa.

According to one embodiment of either Formula Ia or Formula IIa, each of $X_1$, $X_2$, $X_3$, $X_4$, $X_5$, $X_6$, $X_7$ and $X_8$ is an oxygen atom. According to another embodiment, each occurrence of R is —$R_1$—Ar—. According to another embodiment, Each Ar ring is independently substituted with at least one halogen atom. In another embodiment each Ar ring is ortho-substituted with two iodine atoms. Furthermore, each $R_1$ may be an alkyl group containing from one to ten carbon atoms, with a preferred embodiment of two carbon atoms. In another embodiment of Formula Ia, f=1 and both R groups have pendant carboxylate or carboxylic acid groups. In another embodiment of Formula IIa, f=1 and both R groups have pendant amino or backbone imine groups. The pendant amino groups of Formula IIa may be unsubstituted, mono-substituted or di-substituted. Amine substituent embodiments include alkyl groups containing up to 30 carbon atoms, including crystallizable groups containing from 6 to 30 carbon atoms. The number of carbon atoms in the pendant group is in addition to the number of carbon atoms of the R group.

In further embodiments of both Formula Ia and Formula IIa, B is a methylene group or a methyl-substituted methylene group. In another embodiment, the hydroxyl endcapped macromer block comprises at least one macromer block selected from a hydroxy endcapped polycaprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone. In a further embodiment, the alkylene diol is hexane diol.

With further reference to both Formula Ia and Formula IIa, in one embodiment the macromer dicarboxylate block comprises at least one macromer block selected from a polycaprolactone dicarboxylate, a polylactic acid dicarboxylate, a polyglycolic acid dicarboxylate, a poly(lactic acid-co-glycolic acid) dicarboxylate, a poly(alkylene diol) dicarboxylate, a poly(alkylene oxide) dicarboxylate and a polydioxanone dicarboxylate. In a further embodiment, the alkylene diol is hexane diol. The macromer block may be a homopolymer or the macromer block may be co-polymerized, for example, with phosgene, to form a carbonate macromer dicarboxylate.

When $R_5$ and $R_6$ of the Formula Ia and Formula IIa compounds are alkyl, the compounds are not monomers but serve other potential end-uses where a non-reactive compound is desired, particularly when the compounds are radio-opaque.

Each of the foregoing compounds of Formula Ia or Formula IIa may be adapted as a repeating unit in a polymeric composition having the structure of Formula Ib or Formula IIb:

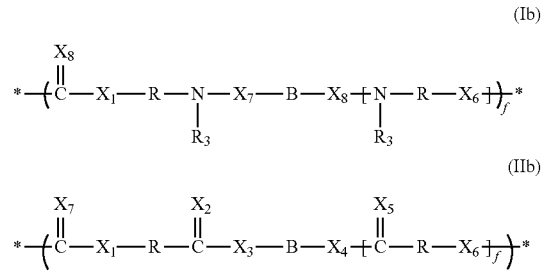

wherein f is 0 or 1, $X_1$, $X_2$, $X_3$, $X_4$, $X_5$, $X_6$, $X_7$ $X_8$, R and B, and the preferred species thereof, are the same as described above with respect to Formula Ia or Formula IIa.

Polymers according to Formula Ib and Formula IIb include block copolymers with a hydroxy endcapped macromer, a mercapto endcapped macromer or an amino endcapped macromer. In one embodiment, the hydroxy endcapped macromer block comprises at least one macromer block selected from a hydroxy endcapped polycaprolactone, a hydroxy endcapped polylactic acid, a hydroxy endcapped polyglycolic acid, a hydroxy endcapped poly(lactic acid-co-glycolic acid), a hydroxy endcapped poly(alkylene diol), a poly(alkylene oxide) and a hydroxy endcapped polydioxanone. In a further embodiment, the alkylene diol is hexane diol. The macromer block may be a homopolymer or the macromer block may be copolymerized, for example with phosgene to form a hydroxy endcapped marcromer carbonate.

While not limited thereto, macromer block copolymers of Formula Ib and Formula IIb may contain from about 25 to about 99 weight percent of macromer blocks.

Those skilled in the art will recognize from the teachings provided herein that the depicted subunits are not recurring units per se, because it will be recognized that there are additional linkages present, and thus depiction of the subunits in this way is not to be construed as an indication that they are connected to one another in an end-to-end fashion without the other linkages described herein. For example, the Formula Ib and Formula IIb polymers also include polycarbonates, polyesters, polyphosphazines, polyphosphoesters and polyiminocarbonates. To this end, polymers having the structures of Formula Ib and Formula IIb include polymers having the structure of Formula Ic and Formula IIc:

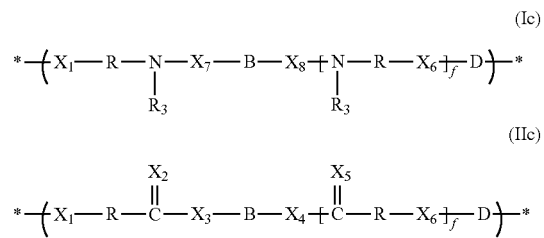

wherein D is selected from

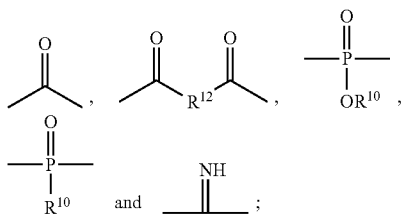

wherein $R^{10}$ is selected from H, an optionally substituted alkyl group, an optionally substituted heteroalkyl group, an optionally substituted alkenyl group and an optionally substituted heteroalkenyl group, each optionally crystallizable and containing from one to 30 carbon atoms, and $R^{12}$ is selected from an optionally a bond, a substituted alkyl group, an optionally substituted heteroalkyl group, an optionally substituted alkenyl group and an optionally substituted heteroalkenyl group, each containing from one to 18 carbon atoms and an optionally substituted alkylaryl group, an optionally substituted heteroalkylaryl group, an optionally substituted alkenylaryl group and optionally substituted heteroalkenylary group, each containing from three to 12 carbon atoms.

D is additionally defined such that $HX_6$-D-$X_1H$ defines an alkylene diol containing up to 24 carbon atoms, an alkylene diamine containing up to 24 carbon atoms, an alkylene dimercaptan containing up to 24 carbon atoms; or a hydroxy endcapped macromer, a mercapto endcapped macromer or an amine endcapped macromer as previously defined.

In accordance with another embodiment, monomeric compounds of any of the foregoing may be polymerized so as to form a polymer or co-polymer with repeating units of any one or more of these monomers. After polymerization, appropriate work up of the polymers in accordance with preferred embodiments of the present invention may be achieved by any of a variety of known methods commonly employed in the field of synthetic polymers to produce a variety of useful articles with valuable physical and chemical properties, all derived from tissue compatible monomers. The useful articles can be shaped by conventional polymer thermoforming techniques such as extrusion and injection molding when the degradation temperature of the polymer is above the glass transition or crystalline melt temperature, or conventional non-thermal techniques can be used, such as compression molding, injection molding, solvent casting, spin casting, wet spinning. Combinations of two or more methods can be used. Shaped articles prepared from the polymers are useful, inter alia, as degradable biomaterials for medical implant applications.

In accordance with the discussion here, medical devices are provided comprising polymers disclosed herein, which are well-suited for use in producing a variety of resorbable medical devices or other implantable devices. Representative device embodiments include stents, disks, plugs, sutures, staples, clips, surgical adhesives, screws, anchors and the like. These and other similar implantable medical devices are preferably radiopaque, biocompatible, and have various times of bioresorption. To this end, the polymers may be further suitable for use in resorbable implantable devices with and without therapeutic agents, device components and/or coatings with and without therapeutic agents for use in other medical systems.

Other resorbable devices that can be advantageously formed from the polymers disclosed herein, and which serve as representative embodiments of useful medical devices, include devices for use in tissue engineering, dental applications, embolotherapy products for the temporary and therapeutic restriction or blocking of blood supply to treat tumors and vascular malformations, and controlled release therapeutic agent delivery devices, as discussed herein.

Another embodiment provides a method of treating a body lumen, by deploying within the body lumen a stent according to a medical device embodiment of the present invention.

Based on the foregoing, additional embodiments of the compounds, monomers, and polymers of the present invention are discussed herein and will be apparent to one of ordinary skill in the art.

DETAILED DESCRIPTION OF THE INVENTION

Novel classes of compounds, monomers, polymers and co-polymers are provided, polymerized from at least one or more repeatable units of compounds and analogs of compounds that naturally occur in the human body.

ABBREVIATIONS AND NOMENCLATURE

The following paragraphs provide definitions of various terms used herein.

As used herein, the terms "macromer," "macromeric" and similar terms have the usual meaning known to those skilled in the art and thus may be used to refer to oligomeric and polymeric materials that are functionalized with end groups that are selected so that the macromers can be copolymerized with other monomers. A wide variety of macromers and methods for making them are known to those skilled in the art. Examples of suitable macromers include hydroxy end-capped polylactic acid macromers, hydroxy endcapped polyglycolic acid macromers, hydroxy endcapped poly(lactic acid-co-glycolic acid) macromers, hydroxy endcapped polycaprolactone macromers, poly(alkylene diol) macromers, hydroxy end-capped poly(alkylene oxide) macromers and hydroxy endcapped polydioxanone macromers.

As used herein, the terms "polymer," "polymeric" and similar terms have the usual meaning known to those skilled in the art and thus may be used to refer to homopolymers, copolymers (e.g., random copolymer, alternating copolymer, block copolymer, graft copolymer) and mixtures thereof.

The term "thermal transition temperature" has the usual meaning known to those skilled in the art and thus may be used to refer to both first order thermal transitions and second order thermal transitions. The first order thermal transition of a polymer or phase thereof may be referred to herein as a "melting point" or Tm", and the second order thermal transition of a polymer or phase thereof may be referred to herein as a "glass transition temperature" or "Tg." Those skilled in the art will appreciate that a polymeric material or phase thereof may have exhibit either or both types of thermal transitions, as well as higher order thermal transitions. Thermal transition temperature may be determined by methods known to those skilled in the art, such as by DSC, DMA, DEA and TMA.

As used herein, the phrase "fracture toughness" means the resistance of a polymer under a static or dynamic load (or strain) to brittle failure from crack propagation within a glassy or semicrystalline phase.

The terms "radiopaque," "radio-opaque," "radiopacity," "radio-opacity," "radiopacifying" and similar terms have the usual meaning known to those skilled in the art and thus may be used to refer to polymer compositions that have been rendered easier to detect using medical imaging techniques (e.g., by X-ray and/or during fluoroscopy) being the incorporation of heavy atoms into the polymer composition. Such incorporation may be by mixing, e.g., by mixing an effective amount of a radiopacifying additive such as barium salt or complex, and/or by attachment of effective amounts of heavy atoms to one or more of the polymers in the polymer composition. For example, attachment of heavy atoms to a polymer in sufficient amounts may advantageously render the polymer easier to detect by various medical imaging techniques. The term "heavy atom" is used herein to refer to atoms having an atomic number of 17 or greater. Preferred heavy atoms have an atomic number of 35 or greater, and include bromine, iodine, bismuth, gold, platinum tantalum, tungsten, and barium. In certain configurations, polymer compositions may be inherently radiopaque. The term "inherently radiopaque" is used herein to refer to a polymer to which a sufficient number of heavy atoms are attached by covalent or ionic bonds to render the polymer radiopaque. This meaning is consistent with the understanding of those skilled in the art, see, e.g., U.S. Patent Publication No. 2006/0024266, which is hereby incorporated by reference for all purposes, including for the particular purpose of describing radiopaque polymeric materials.

The terms "alkyl", "alkylene" and similar terms have the usual meaning known to those skilled in the art and thus may be used to refer to straight or branched hydro-carbon chain fully saturated (no double or triple bonds) hydrocarbon group. Terminal alkyl groups, e.g., of the general formula $-C_nH_{2n+1}$, may be referred to herein as "alkyl" groups, whereas linking alkyl groups, e.g., of the general formula $-(CH_2)_n-$, may be referred to herein as "alkylene" groups. The alkyl group may have 1 to 50 carbon atoms (whenever it appears herein, a numerical range such as "1 to 50" refers to each integer in the given range; e.g., "1 to 50 carbon atoms" means that the alkyl group may consist of 1 carbon atom, 2 carbon atoms, 3 carbon atoms, etc., up to and including 50 carbon atoms, although the present definition also covers the occurrence of the term "alkyl" where no numerical range is designated). The alkyl group may also be a medium size alkyl having 1 to 30 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

The alkyl group may be substituted or unsubstituted. When substituted, the substituent group(s) is(are) one or more group(s) individually and independently selected from lower alkyl, alkenyl, alkynyl, cycloalkyl, cycloalkenyl, cycloalkynyl, aryl, hydroxyaryl, heteroaryl, heteroalicyclyl, aralkyl, heteroaralkyl, (heteroalicyclyl)alkyl, hydroxy, protected hydroxyl, alkoxy, aryloxy, acyl, carboxyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, iso-thiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and protected derivatives.

The terms "alkenyl," "alkenylene" and similar terms have the usual meaning known to those skilled in the art and thus may be used to refer to an alkyl or alkylene group that contains in the straight or branched hydrocarbon chain one or more double bonds. An alkenyl group may be unsubstituted or substituted. When substituted the substituent(s) may be selected from the same groups disclosed above with regard to alkyl group substitution unless otherwise indicated.

The terms "heteroalkyl," "heteroalkylene" and similar terms have the usual meaning known to those skilled in the art and thus may be used to refer to an alkyl group or alkylene group as described herein in which one or more of the carbons atoms in the backbone of alkyl group or alkylene group has been replaced by a heteroatom such as nitrogen, sulfur and/or oxygen. Likewise, the term "heteroalkenylene" may be used to refer to an alkenyl or alkenylene group in which one or more of the carbons atoms in the backbone of alkyl group or alkylene group have been replaced by a heteroatom such as nitrogen, sulfur and/or oxygen.

The term "aryl" has the usual meaning known to those skilled in the art and thus may be used to refer to a carbocyclic (all carbon) monocyclic or multicyclic aromatic ring system that has a fully delocalized pi-electron system. Examples of aryl groups include, but are not limited to, benzene, naphthalene and azulene. The ring of the aryl group may have 5 to 50 carbon atoms. The aryl group may be substituted or unsubstituted. When substituted, hydrogen atoms are replaced by up to four substituent group(s) per aromatic ring that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thio-carbamyl, C-amido, N-amido, S-sulfonamido, N-sulfonamido, C-carboxy, protected C-carboxy, O-carboxy, isocyanato, thiocyanato, iso-thiocyanato, nitro, silyl, sulfenyl, sulfinyl, sulfonyl, haloalkyl, haloalkoxy, trihalomethanesulfonyl, trihalomethanesulfon-amido, and amino, including mono- and di-substituted amino groups, and the protected derivatives thereof, unless the substituent groups are otherwise indicated. An aryl group substituted with alkyl may be referred to herein as "alkylaryl."

The term "heteroaryl" has the usual meaning known to those skilled in the art and thus may be used to refer to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The ring of the heteroaryl group may have 5 to 50 atoms. The heteroaryl group may be substituted or unsubstituted. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

The term "crystallizable" has the usual meaning known to those skilled in the art, see U.S. Patent Publication No. 20060024266, which is incorporated herein by reference for all purposes and particularly for the purpose of describing crystallizable groups. Polymers that contain crystallizable groups that are attached to the sides of the polymer, known as side chain crystallizable (SCC) polymers or "comb-like" polymers, are well-known, see N. A. Plate and V. P. Shibaev, J. Polymer Sci.: Macromol. Rev. 8:117-253 (1974), the disclosure of which is hereby incorporated by reference.

In an embodiment, a polymer as described herein contains crystallizable side groups and thus may be regarded as a SCC polymer. It will be understood that the crystallizable side chains of SCC polymers are preferably selected to crystallize with one another to form crystalline regions and may comprise, for example, —$(CH_2)_x$— and/or $((CH_2)_b$—O—$)_y$ groups. The side chains are preferably linear to facilitate crystallization. For SCC polymers that contain —$(CH_2)_x$— groups in the crystallizable side chain, x is preferably in the range of about 6 to about 30, more preferably in the range of about 20 to about 30. For SCC polymers that contain —$((CH_2)_y$—O—$)_x$ groups in the crystallizable side chain, x is preferably in the range of about 6 to about 30 and y is preferably in the range of about 1 to about 8. More preferably, x and y are selected so that the $((CH_2)_y$—O—$)_x$ groups contain from about 6 to about 30 carbon atoms, even more preferably from about 20 to about 30 carbon atoms. The spacing between side chains and the length and type of side chain are preferably selected to provide the resulting SCC polymer with a desired melting point. As the spacing between side chains increases, the tendency for the side chains to be crystallizable tends to decrease. Likewise, as the flexibility of the side chains increases the tendency for the side chains to be crystallizable tends to decrease. On the other hand, as the length of the side chains increases, the tendency for the side chains to be crystallizable tends to increase. In many cases, the length of the crystallizable side chain may be in the range of about two times to about ten times the average distance between crystallizable side chains of the SCC polymer.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents.

Unless otherwise indicated, when a substituent is deemed to be "optionally substituted," or "substituted" it is meant that the substituent is a group that may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxy, alkoxy, aryloxy, acyl, ester, mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. Similarly, the term "optionally ring-halogenated" may be used to refer to a group that optionally contains one or more (e.g., one, two, three or four) halogen substituents on the aryl and/or heteroaryl ring. The protecting groups that may form the protective derivatives of the above substituents are known to those of skill in the art and may be found in references such as Greene and Wuts, Protective Groups in Organic Synthesis, 3$^{rd}$ Ed., John Wiley & Sons, New York, N.Y., 1999, which is hereby incorporated by reference in its entirety.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound having one or more double bond(s) generating geometrical isomers that can be defined as E or Z each double bond may independently be E or Z a mixture thereof. Likewise, all tautomeric forms are also intended to be included.

As used herein, the abbreviations for any protective groups, amino acids and other compounds are, unless indicated otherwise, in accord with their common usage, recognized abbreviations, or the IUPAC-IUP Commission on Biochemical Nomenclature (See, Biochem. 11:942-944 (1972)).

Polymer Compositions and Methods

The monomers and polymers of the present invention are derivatives of amino acids and analogs thereof. Examples of such compounds include 2-amino-3-(4-hydroxyphenyl)-propenoic acid (a cinnamic acid derivative), 2,2-amino-(4-hydroxy-phenyl)ethanoic acid, 2-amino-3-(4-hydroxy-phenyl)propanoic acid (tyrosine), 2-amino-4-(4-hydroxyphenyl)butanoic acid, 2,2-amino-(5-hydroxy-1H-indol-3-yl)ethanoic acid, 2-amino-3-(5-hydroxy-1H-indol-3-yl)propanoic acid (5-hydroxy-tryptophan), 2-amino-4-(5-hydroxy-1H-indol-3-yl)butanoic acid, 2,2-amino-(4-hydroxyphenoxy-phenyl)ethanoic acid, 2-amino-3-(4-hydroxy-phenoxy-phenyl)propanoic acid (thyronine), 2-amino-4-(4-hydroxy-phenoxy-phenyl)butanoic acid, and the like. Amino acids from which monomers and polymers may be derived in which the "X" groups are all oxygens have the structure:

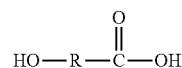

Wherein R and the preferred species thereof, are the same as described above with respect to Formula IIa.

Monomers and polymers derived from cysteine, serine, threonine, tyrosine, thyronine, hydroxy-tryptophan, and the like, and the iodinated form of thyronine, thyroxine, are preferred, but not necessarily limiting to the present invention. In accordance with the foregoing, tyrosine and hydroxyl-tryptophan may also be substituted at aromatic ring positions with a bromine or iodine, or any other similar element or compound adapted to provide for a radio-opaque quality. Serine, tyrosine, thyronine, thyroxine and hydroxy-tryptophan embodiments degrade to form compounds naturally found in the body or closely-related analogs thereof. In addition to being non-toxic, the aromatic rings of tyrosine, thyronine, thyroxine and hydroxy-tryptophan impart good mechanical properties to polymers.

Formula Ia compounds are prepared by reacting either approximately one mole (f=0) or approximately two moles (f=1) of one or more carboxy-protected compounds with the structure of Formula Id:

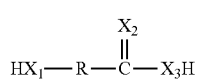
(Id)

with phosgene or triphosgene and approximately one mole of a compound having the structure of Formula Ie:

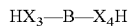 (Ie).

wherein $X_1$, $X_2$, $X_3$, $X_4$, and B, and the preferred species thereof, are the same as previously described, and R is the same as described with respect to Formula Ib.

Formula IIa compounds are prepared by reacting amine-protected compounds of Formula Id with one to two moles of the Formula Ic compounds. When the Formula Id compound is an aromatic amino acid such as tyrosine, thyronine thyroxine or hydroxy-tryptophan, and the Formula Ie compound is a diol, the two compounds are reacted in an acid catalyzed Fischer Esterification reaction as follows:

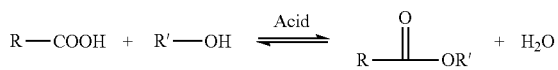

Because this reaction is reversible, removing water from the reaction mixture shifts the equilibrium to the right. Water removal is usually accomplished by way of azeotropic distillation; however other techniques known in the art may be employed as well. In instances where azeotropic distillation is desired, the solvent used for the reaction is carefully chosen so that it forms an azeotropic mixture with water. Generally, solvents such as toluene, heptane, chloroform, tetrachloethylene are preferred.

The main advantage of this reaction is that primary and secondary alcohols form esters with carboxylic acids under acid catalysis, whereas aromatic ring hydroxy groups are non-reactive under these conditions. The carboxylic acid groups of Formula Id can be reacted with primary or secondary alcohols while the phenolic groups remain intact.

When the Formula Ia or Formula IIa compound is a tyrosine, thyronine, thyroxine or hydroxyl-tryptophan, the Formula Ia and Formula IIa compounds contain diphenolic and other aromatic hydroxyl groups that can be polymerized, for example into polycarbonates by reaction with phosgene. When radiopaque embodiments are reacted with PLA, PGA or PLGA, the polymer obtained is a radio-opaque copolymer of PLA, PGA or PLGA.

In certain embodiments, some of the macromer-diols such as hydroxy endcapped polycaprolactone-diol and poly(ethylene glycol) are commercially available. In some cases when such macromer diols as in the case poly(lactic acid)-diol were not available, they were prepared using an alkane diol as the initiator.

In further embodiments, B of Formula IIa is comprised of an macromeric alkyl group of a straight or branched chain alkyl group containing from 1 to 18 carbon atoms. In more specific embodiments, n is 3, 4, 5 or 6.

New Formula Ib and IIb polymers may be formed from the Formula Ia and IIa monomers of the present invention, in the same fashion as the desaminotyrosyl-tyrosine alkyl ester-derived polymers disclosed before. In one embodiment the Formula IIa diphenol monomers may be polymerized to form a polycarbonate, polyester, poly(phosphazine), poly (phosphoester) or poly(iminocarbonate). This embodiment may be represented by Formula Ic and Formula IIc:

(Ic)

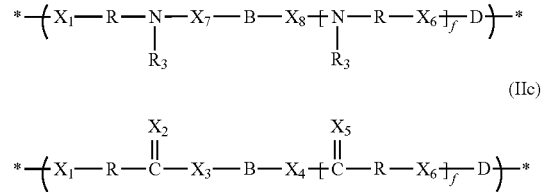
(IIc)

wherein each of f, $X_1$, $X_2$, $X_3$, $X_4$, $X_5$, $X_6$, $X_7$, $X_8$, R and B, and the preferred embodiments thereof, are the same as described above and D is selected from:

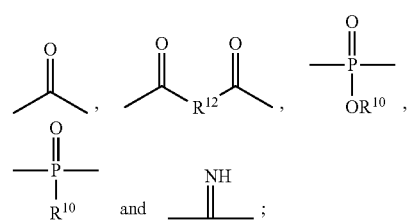

wherein $R^{10}$ is selected from H, an optionally substituted alkyl group, an optionally substituted heteroalkyl group, an optionally substituted alkenyl group and an optionally substituted heteroalkenyl group, each optionally crystallizable and containing from one to 30 carbon atoms, and $R^{12}$ is selected from a bond, an optionally substituted alkyl group, an optionally substituted heteroalkyl group, an optionally substituted alkenyl group and an optionally substituted heteroalkenyl group, each containing from one to 18 carbon atoms and an optionally substituted alkylaryl group, an optionally substituted heteroalkylaryl group, an optionally substituted alkenylaryl group and an optionally substituted heteroalkenylary group, each containing from three to 12 carbon atoms. One of ordinary skill in the art will understand that the placement of D in a position adjacent to $X_6$ is not limiting to the present invention and that D may also be positioned adjacent to $X_1$ to achieve similar effects, as discussed herein.

Based on the foregoing, in certain embodiments of Formula IIc, D is a carboxy group having the following structure:

wherein the carboxy group is derived from a phosgene starting material. This method is essentially the conventional method for polymerizing diols into polycarbonates. Suitable processes, associated catalysts and solvents are known in the art and are taught in Schnell, Chemistry and Physics of Polycarbonates, (Interscience, New York 1964), the teachings of which are also incorporated herein by reference. Because $X_1$ and $X_6$ are independently selected from O, S and $NR_3$, the reaction of the formula III monomers with phosgene may also produce urea linkages (—$NR_3$—(C=O)—$NR_3$—), carbonodithioate linkages (—S—(C=O)—S—), carbamate linkages (—O—(C=O)—$NR_3$—), thiocarbonate linkages (—S—(C=O)—O—) and thiocarbamate linkages (—S—(C=O)—$NR_3$—). Other methods adaptable for use to prepare the polycarbonate and other phosgene-derived polymers of the present invention are disclosed in U.S. Pat. Nos. 6,120,491, and 6,475,477 the disclosures of which are incorporated by reference.

In another embodiment, D of Formula IIc is a group having the structure:

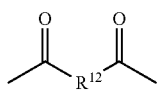

which is derived from a carboxylic acid starting material. When the monomer of Formula IIa is a diphenol, the Formula IIc polymer is formed by reaction of the diphenol with an aliphatic or aromatic dicarboxylic acids in the carbodiimide mediated process disclosed by U.S. Pat. No. 5,216,115 using 4-(dimethylamino) pyridinium-p-toluene sulfonate (DPTS) as a catalyst. The disclosure of U.S. Pat. No. 5,216,115 is incorporated by reference.

The foregoing process forms polymers with —O—C(=O)—$R_{12}$—C(=O)—O— linkages. $R_{12}$ may be selected so the dicarboxylic acids employed as starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R_{12}$ may be —$CH_2$—$CH_2$—C(=O)—, —$CH_2$—$CH_2$—, —CH=CH— and —$CH_2$—C(=O)—, respectively).

Yet another naturally-occurring aliphatic dicarboxylic acid is adipic acid ($R_{12}$ is (—$CH_2$—)$_4$), found in beet juice. Still another biocompatible aliphatic dicarboxylic acid is sebacic acid ($R_{12}$ is (—$CH_2$—)$_8$), which has been studied extensively and has been found to be nontoxic as part of the clinical evaluation of poly(bis(p-carboxyphenoxy)propane-co-sebacic acid anhydride) by Laurencin et al., J. Biomed. Mater. Res., 24, 1463-81 (1990).

Other biocompatible aliphatic dicarboxylic acids include oxalic acid. Oxalic acid is known to lose CO and react effectively in an identical fashion to phosgene leaving a "CO" group or a carbamate with reaction with two alcohol groups, in which case $R_{12}$ is a bond,

malonic acid ($R_{12}$ is —$CH_2$—), glutaric acid ($R_{12}$ is (—$CH_2$—)$_3$), pimelic acid ((—$CH_2$—)$_5$), suberic acid ($R_{12}$ is (—$CH_2$—)$_6$) and azelaic acid ($R_{12}$ is (—$CH_2$—)$_7$). $R_{12}$ can thus represent (—$CH_2$—)$_Q$, where Q is between 0 and 8, inclusive. Among the suitable aromatic dicarboxylic acids are terephthalic acid, isophthalic acid and bis(p-carboxyphenoxy) alkanes such as bis(p-carboxy-phenoxy) propane.

$R_{12}$ can also have the structure:

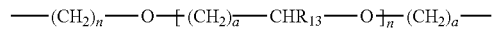

wherein a is 1, 2 or 3, inclusive, n is from 1 to 500,000, inclusive, and $R_{13}$ is hydrogen or a lower alkyl group containing from one to four carbon atoms. $R_{13}$ is preferably hydrogen, a is preferably 1, and n is preferably between about 10 and about 100, and more preferably between about 10 and about 50.

$R_{12}$ can also have the structure:

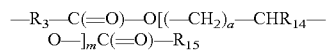

wherein a, m and $R_{14}$ and the preferred species thereof are the same as described above. $R_{15}$ is selected from a bond or straight and branched alkyl and alkylaryl groups containing up to 18 carbon atoms.

The compounds of Formulae Id and Ie, when the amino, carboxylate and other reactive groups of R are appropriately protected, react with phosgene or triphosgene to form the compounds of Formula IIIa:

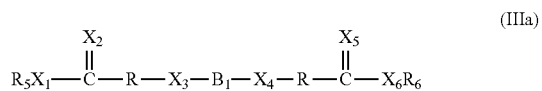

(IIIa)

wherein $X_1$, $X_2$, $X_3$, $X_4$, $X_5$ and $X_6$ are independently selected from O, S and $NR_3$ wherein $R_3$ is selected from the group consisting of hydrogen and alkyl groups containing from one to six carbon atoms. Each R is independently selected from optionally substituted aromatic, heteroaromatic, aryl ether, haloaromatic alkyl, heteroalkyl, alkenyl and heteroalkenyl groups, each containing from one to ten carbon atoms. The number of carbon atoms in any pendant group of R is in addition to the number of carbon atoms of the R group. $R_5$ and $R_6$ are independently selected from hydrogen and an alkyl group containing from one to six carbon atoms.

In an embodiment at least one R is —$R_1$—Ar— or —Ar—$R_1$— and Ar, $R_1$, $R_5$, $X_1$, $X_2$, $X_5$, $X_6$ and $R_6$ are selected so at least one of $R_5$—$X_1$—R—(C=$X_2$)OH and HO—(C=$X_5$)—R—$X_6$—$R_6$ is $R_5$—$X_1$—Ar—$R_1$—(C=$X_2$)OH or HO—(C=$X_5$)—$R_1$—Ar—$X_6$—$R_6$, respectively, wherein each Ar is independently selected from the group consisting of phenyl,

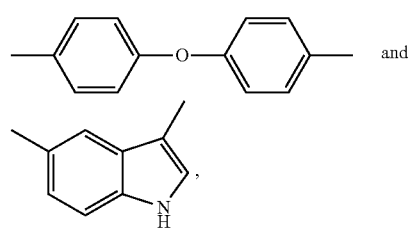

optionally substituted with from one to four substituents per aromatic ring independently selected from the group consisting of halogen, halomethyl, halomethoxy, methyl, methoxy, thiomethyl, nitro, sulfoxide, and sulfonyl.

Each $R_1$ is independently selected from optionally substituted aromatic, heteroaromatic, aryl ether, haloaromatic alkyl, heteroalkyl, alkenyl and heteroalkenyl groups containing from one to ten carbon atoms; and $B_1$ is a carboxy group.

The Formula IIIa monomers are polymerized according to conventional dicarboxylate polymerization processes to form polyesters, polyamides, and the like, and the sulfur and amino analogs thereof, having the structure of Formula IIIb:

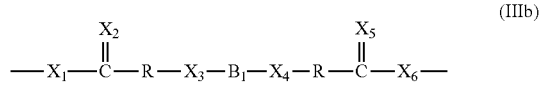

(IIIb)

wherein each of $X_1$, $X_2$, $X_3$, $X_4$, $X_5$, $X_6$, R and $B_1$, and the embodiments thereof, are the same as described above for Formula IIIa.

Polymers according to Formula Ib, Formula IIb and Formula IIIb include block copolymers with a hydroxy endcapped macromer, a mercapto endcapped macromer or an amino endcapped macromer. Macromer blocks are selected that are also reactive with the co-monomer with which the Formula Ia, Formula IIa or Formula IIIa monomer is being copolymerized. For example, a hydroxy endcapped macromer can be added to the reaction between a Formula Ia or a Formula IIa diphenol and phosgene to form a polycarbonate macromer block copolymer, or it can be added to the reaction between a Formula IIa diphenol and a dicarboxylic acid to form a polyarylate macromer block copolymer.

Molar fractions of macromer units range from greater than zero to less than one and are typically greater than zero up to about 0.5. Embodiments include an macromer molar fraction between about 0.10 and about 0.25.

Formula Ia include carboxylic acid monomer compounds that can be adapted to provide polymers among the embodiments disclosed herein having pendant free carboxylic acid groups. However, it is difficult to prepare polymers having pendent free carboxylic acid groups by polymerization of corresponding monomers with pendent free carboxylic acid groups without cross-reaction of the free carboxylic acid group with the co-monomer. Accordingly, polymers having pendent free carboxylic acid groups are preferably prepared from the corresponding benzyl and tert-butyl ester polymers.

The benzyl ester polymers may be converted to the corresponding free carboxylic acid polymers through the selective removal of the benzyl groups by the palladium catalyzed hydrogenolysis method disclosed in U.S. Pat. No. 6,120,491, the disclosure of which is incorporated herein by reference, and particularly for the purpose of describing such methods. The tert-butyl ester polymers may be converted to the corresponding free carboxylic acid polymers through the selective removal of the tert-butyl groups by the acidolyis method disclosed in U.S. Patent Publication No. 20060034769, also incorporated herein by reference, and particularly for the purpose of describing such methods. The catalytic hydrogenolysis or acidolysis is preferable because the lability of the polymer backbone tends to discourage the employment of harsher hydrolysis techniques.

The molar fraction of free carboxylic acid units in the polymers described herein can be adjusted to modify the degradation of devices made from such polymers. For example, polymers with lower amounts of free carboxylic acid will tend to have longer lifetimes in the body. Further, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are desirable or required.

The pendant amino and carboxylic acid groups of the Formula Ia and IIa monomers and the Formula Ib, Ic, IIb and IIc polymers may be derivatized by covalent attachment of a therapeutic agent. Depending on the moieties present on the underivatized therapeutic agent the covalent bond may be an amide or ester bond. Typically the therapeutic agent is derivatized at a primary or secondary amine, hydroxy, ketone, aldehyde or carboxylic acid group. Chemical attachment procedures are described by U.S. Pat. Nos. 5,219,564 and 5,660,822; Nathan et al., Bio. Cong. Chem., 4, 54-62 (1993) and Nathan, Macromol., 25, 4476 (1992), all of which are incorporated by reference, and particularly for the purpose of describing such procedures.

The therapeutic agent may first be covalently attached to a monomer, which is then polymerized, or the polymerization may be performed first, followed by covalent attachment of the therapeutic agent. Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymers described herein using conventional techniques well-known to those of ordinary skill in the art. For this therapeutic agent delivery embodiment, it is not essential that the polymer have pendent groups for covalent attachment of the therapeutic agent.

Polymers with a sufficient number of aromatic rings that are sufficiently substituted with bromine or iodine are inherently radiopaque. Various aromatic rings in both the first polymer phase and the second polymer phase can be iodine or bromine substituted. For example, independent of any particular polymer embodiment, the aromatic rings of the recurring units of the formula (I) may be substituted with at least one iodine or bromine atom, on at least one and preferably on both ring positions. In an embodiment, at least 50% of the aromatic rings of recurring units of the formula (I) in a polymer composition are substituted with from two to four iodine or bromine atoms.

The radiopaque monomers may be prepared according to the disclosure of U.S. Pat. No. 6,475,477, or the disclosure of U.S. Patent Publication No. 2006/0034769, the disclosures of both of which are incorporated herein by reference, and particularly for the purpose of describing such monomers and methods of making them. The iodinated and brominated phenolic monomers described herein can also be employed as radiopacifying, biocompatible non-toxic additives for biocompatible polymer compositions, as provided herein. Iodinated and brominated polymers may be polymerized from iodinate and brominated monomers, or the polymers can be iodinated or brominated after polymerization.

In another radiopaque polymer embodiment, methylene hydrogens are replaced with bromine or iodine to increase polymer radio-opacity. Such substitution may be concurrent with or in place of halogen substituted phenyl groups, as discussed above. Accordingly, radio-opaque polylactic acids, polyglycolic acids and polylactic-co-glycolic acids are provided by replacing a sufficient number of methylene hydrogens with bromine, iodine or both. A preferred radio-opaque polylactic acid contains lactic acid units with pendant tri-iodomethyl groups.

Polymers and monomers with imine backbones are prepared by methods disclosed by U.S. Provisional Application Ser. No. 61/250,545, filed on the same date as the present application, the disclosure of which is incorporated herein by reference, and particularly for the purpose of describing such methods. More specifically, polymers and monomers derived from alpha-amino acids may be reacted with phosgene or triphosgene in pyridine to form an imino group. In monomer-preparation and polymerization reactions employing phosgene or triphosgene, this is simply a matter of using excess phosgene or triphosgene in the reaction to form the imino group. However, for the preparation of other polymers, the imino group must be formed in advance on the monomer.

After polymerization of any of the foregoing compounds or monomers, appropriate work up of the polymers in accordance with preferred embodiments of the present invention may be achieved by any of a variety of known methods commonly employed in the field of synthetic polymers to produce a variety of useful articles with valuable physical and chemical properties.

Medical Uses

Various embodiments of the polymer compositions described herein, preferably derived from tissue compatible monomers, may be used to produce a variety of useful articles with valuable physical and chemical properties. The useful articles can be shaped by conventional polymer thermo-forming techniques such as extrusion and injection molding when the degradation temperature of the polymer is above the glass transition or crystalline melt temperature(s), or conventional non-thermal techniques can be used, such as compression molding, injection molding, solvent casting, spin casting, wet spinning. Combinations of two or more methods can be used. Shaped articles prepared from the polymers are useful, inter alia, as biocompatible, biodegradable and/or bioresorbable biomaterials for medical implant applications.

In one embodiment, the medical device is a stent. It is contemplated that a stent may comprise many different types of forms. For instance, the stent may be an expandable stent. In another embodiment, the stent may be configured to have the form of a sheet stent, a braided stent, a self-expanding stent, a woven stent, a deformable stent, or a slide-and-lock stent. Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms.

In certain other embodiments, the polymers are formed into coatings on the surface of an implantable device, particularly a stent, made either of a polymer of the present invention or another material, such as metal. Such coatings may be formed on stents via techniques such as dipping, spray coating, combinations thereof, and the like. Further, stents may be comprised of at least one fiber material, curable material, laminated material, and/or woven material. The medical device may also be a stent graft or a device used in embolotherapy.

Details of stent products and fabrication in which the polymers of the present invention may be employed are disclosed in U.S. Patent Publication No. 2006/0034769, the disclosure of which is incorporated by reference. Stents are preferably fabricated from the radiopaque polymers of the present invention, to permit fluoroscopic positioning of the device.

The highly beneficial combination of properties associated with the polymers disclosed herein means these polymers are well-suited for use in producing a variety of resorbable medical devices besides stents, especially implantable medical devices that are preferably radiopaque, biocompatible, and have various times of bioresorption. For example the polymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

The polymers described herein can thus be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lungtrachea/bronchus stents, and the like.

In addition, the resorbable polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that the resorbable polymers disclosed herein are well-suited for use in producing a variety of coatings for medical devices, especially implantable medical devices.

In some embodiments, the disclosed polymers may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices that can be advantageously formed from preferred embodiments of the polymers described herein include devices for use in tissue engineering. Examples of suitable resorbable devices include tissue engineering scaffolds and grafts (such as vascular grafts, grafts or implants used in nerve regeneration). The present resorbable polymers may also be used to form a variety of devices effective for use in closing internal wounds. For example biodegradable resorbable sutures, clips, staples, barbed or mesh sutures, implantable organ supports, and the like, for use in various surgery, cosmetic applications, and cardiac wound closures can be formed.

Various devices useful in dental applications may advantageously be formed from disclosed polymer embodiments. For example, devices for guided tissue regeneration, alveolar ridge replacement for denture wearers, and devices for the regeneration of maxilla-facial bones may benefit from being radiopaque so that the surgeon or dentist can ascertain the placement and continuous function of such implants by simple X-ray imaging.

Preferred embodiments of the polymers described herein are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which polymer embodiments described herein may be employed are disclosed in U.S. Patent Publication No. 2005/0106119, the disclosure of which is incorporated by reference. Embolotherapy treatment methods are by their very nature local rather than systemic and the products are preferably fabricated from radiopaque polymers, such as the radiopaque polymers disclosed herein, to permit fluoroscopic monitoring of delivery and treatment.

The polymers described herein are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

A medical device that comprises a polymeric material may include one or more additional components, e.g., a plasticizer, a filler, a crystallization nucleating agent, a preservative, a stabilizer, a photoactivation agent, etc., depending on the intended application. For example, in an embodiment, a medical device comprises an effective amount of at least one therapeutic agent and/or a magnetic resonance enhancing agent. Non-limiting examples of preferred therapeutic agents include a chemotherapeutic agent, a non-steroidal anti-inflammatory, a steroidal anti-inflammatory, and a wound healing agent. Therapeutic agents may be co-administered with the polymeric material. In a preferred embodiment, at least a portion of the therapeutic agent is contained within the polymeric material. In another embodiment, at least a portion of the therapeutic agent is contained within a coating on the surface of the medical device.

Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexamethasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation.

The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For devices placed in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The agent(s) may be selected from the group consisting of antiproliferative agents, anti-inflammatory, anti-matrix metalloproteinase, and lipid lowering, cholesterol modifying, anti-thrombotic and antiplatelet agents, in accordance with preferred embodiments of the present invention. In some preferred embodiments of the stent, the therapeutic agent is contained within the stent as the agent is blended with the polymer or admixed by other means known to those skilled in the art. In other preferred embodiments of the stent, the therapeutic agent is delivered from a polymer coating on the stent surface. In another preferred variation the therapeutic agent is delivered by means of no polymer coating. In other preferred embodiments of the stent, the therapeutic agent is delivered from at least one region or one surface of the stent. The therapeutic may be chemically bonded to the polymer or carrier used for delivery of the therapeutic of at least one portion of the stent and/or the therapeutic may be chemically bonded to the polymer that comprises at least one portion of the stent body. In one preferred embodiment, more than one therapeutic agent may be delivered.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer described herein. Controlled therapeutic agent delivery systems may also be prepared by direct application of the therapeutic agent to the surface of an implantable medical device such as a bioresorbable stent device (comprised of at least one of the polymers described herein) without the use of these polymers as a coating, or by use of other polymers or substances for the coating.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer embodiment. Controlled therapeutic agent delivery systems may also be prepared by direct application of the therapeutic agent to the surface of an implantable medical device such as a bioresorbable stent device (comprised of at least one of the present polymers) without the use of these polymers as a coating, or by use of other polymers or substances for the coating.

The therapeutic agent may first be covalently attached to a monomer, which is then polymerized, or the polymerization may be performed first, followed by covalent attachment of the therapeutic agent. Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymer embodiments using conventional techniques well-known to those of ordinary skill in the art. For this therapeutic agent delivery embodiment, it is not essential that the polymer have pendent groups for covalent attachment of the therapeutic agent.

The polymer compositions described herein containing therapeutic agents, regardless of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

Implantable medical devices may thus be fabricated that also serve to deliver a therapeutic agent to the site of implantation by being fabricated from or coated with the therapeutic agent delivery system embodiment described herein in which a disclosed polymer embodiment has a therapeutic agent physically admixed therein or covalently bonded thereto, such as a drug-eluting stent. Covalent attachment requires a polymer to have a reactive pendant group. Embolotherapeutic particles may also be fabricated for delivery of a therapeutic agent.

Examples of biologically or pharmaceutically active therapeutic agents that may be physically admixed with or covalently attached to polymer embodiments disclosed herein include acyclovir, cephradine, malphalen, procaine, ephedrine, adriamycin, daunomycin, plumbagin, atropine, quinine, digoxin, quinidine, biologically active peptides, chlorin e.sub.6, cephradine, cephalothin, proline and proline analogs such as cis-hydroxy-L-proline, malphalen, penicillin V and other antibiotics, aspirin and other non-steroidal anti-inflammatory compounds, nicotinic acid, chemodeoxycholic acid, chlorambucil, anti-tumor and anti-proliferative agents, including anti-proliferative agents that prevent restenosis, hormones such as estrogen, and the like. Biologically active compounds, for purposes of the present invention, are additionally defined as including cell attachment mediators, biologically active ligands, and the like.

The invention described herein also includes various pharmaceutical dosage forms containing the polymer-therapeutic agent combinations described herein. The combination may be a bulk matrix for implantation or fine particles for administration by traditional means, in which case the dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

The dosage forms may include one or more pharmaceutically acceptable carriers. Such materials are non-toxic to recipients at the dosages and concentrations employed, and include diluents, solubilizers, lubricants, suspending agents, encapsulating materials, penetration enhancers, solvents, emollients, thickeners, dispersants, buffers such as phosphate, citrate, acetate and other organic acid salts, antioxidants such as ascorbic acid, preservatives, low molecular weight (less than about 10 residues) peptides such as polyarginine, proteins such as serum albumin, gelatin, or immunoglobulins, other hydrophilic polymers such as poly(vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counter-ions such as sodium and/or nonionic surfactants such as tween, pluronics or PEG.

Therapeutic agents to be incorporated in the polymer conjugates and physical admixture embodiments disclosed herein may be provided in a physiologically acceptable carrier, excipient stabilizer, etc., and may be provided in sustained release or timed release formulations supplemental to the polymeric formulation prepared in this invention. Liquid carriers and diluents for aqueous dispersions are also suitable for use with the polymer conjugates and physical admixtures.

Subjects in need of treatment, typically mammalian, using the disclosed polymer-therapeutic agent combinations, can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-therapeutic agent combinations may be prepared for storage under conditions suitable for the preservation of therapeutic agent activity as well as maintaining the integrity of the polymers, and are typically suitable for storage at ambient or refrigerated temperatures.

Depending upon the particular compound selected transdermal delivery may be an option, providing a relatively steady delivery of the drug, which is preferred in some circumstances. Transdermal delivery typically involves the use of a compound in solution with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the therapeutic agent to the patient.

The polymer-drug formulation described herein may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally or via inhalation. Therapeutic agent toxicity could thus be reduced by selective delivery to the affected site. For example if the therapeutic agent is liposome encapsulated, and is injected intravenously, the liposomes used are taken up by vascular cells and locally high concentrations of the therapeutic agent could be released over time within the blood vessel wall, resulting in improved action of the therapeutic agent. The liposome encapsulated therapeutic agents are preferably administered parenterally, and particularly, by intravenous injection.

Liposomes may be targeted to a particular site for release of the therapeutic agent. This would obviate excessive dosages that are often necessary to provide a therapeutically useful dosage of a therapeutic agent at the site of activity, and consequently, the toxicity and side effects associated with higher dosages.

Therapeutic agents incorporated into the polymers described herein may desirably further incorporate agents to facilitate their delivery systemically to the desired target, as long as the delivery agent meets the same eligibility criteria as the therapeutic agents described above. The active therapeutic agents to be delivered may in this fashion be incorporated with antibodies, antibody fragments, growth factors, hormones, or other targeting moieties, to which the therapeutic agent molecules are coupled.

The polymer-therapeutic agent combinations described herein may also be formed into shaped articles, such as valves, stents, tubing, prostheses, and the like. Cardiovascular stents may be combined with therapeutic agents that prevent restenosis. Implantable medical devices may be combined with therapeutic agents that prevent infection.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rates from the formulations of this invention are also varied within the routine skill in the art to determine an advantageous profile, depending on the therapeutic conditions to be treated.

A typical dosage might range from about 0.001 mg/kg to about 1,000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

In practicing the methods described herein, the polymer-therapeutic agent combinations may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

An advantage of using the radiopaque, bioresorbable polymers described herein in therapeutic agent delivery applications is the ease of monitoring release of a therapeutic agent and the presence of the implantable therapeutic delivery system. Because the radiopacity of the polymeric matrix is due to covalently attached halogen substituents, the level of radiopacity is directly related to the residual amount of the degrading therapeutic agent delivery matrix still present at the implant site at any given time after implantation. In preferred embodiments the rate of therapeutic release from the degrading therapeutic delivery system will be correlated with the rate of polymer resorption. In such preferred embodiments, the straight-forward, quantitative measurement of the residual degree of radio-opacity will provide the attending physician with a way to monitor the level of therapeutic release from the implanted therapeutic delivery system.

The following non-limiting examples set forth herein below illustrate certain aspects of the invention. All parts and percentages are by mole percent unless otherwise noted and all temperatures are in degrees Celsius unless otherwise indicated. All solvents were HPLC grade and all other reagents were of analytical grade and were used as received, unless otherwise indicated.

EXAMPLES

Example 1: Preparation of Tyrosine Ethyl Ester Diamide with Adipic Acid (TE-AA-TE)

Into a 2 L round-bottomed flask equipped with an overhead stirrer were added 14.6 g (10.0 mmol) of adipic acid, 51.6 g (21.0 mmol) of tyrosine ethyl ester hydrochloride (TE.HCl), 2.84 g (21 mmol) of hydroxybenzotriazole, and 600 mL of dimethylformamide (DMF). The contents of the flask were stirred and the flask was cooled in ice-water to ca 5° C. Triethylamine (21.2 g, 210 mmol) was added with an addition funnel over 5 m. EDCI (44.3 g, 231 mmol) was added to the flask using funnel and 50 mL of DMF was used to wash the funnel into the flask. The reaction mixture was stirred for 1 h at <10° C. and the ice-water bath was removed and then stirred at ambient temperature for 5 h. To the flask was then added 1200 mL of 0.2 M HCl and 400 g of sodium chloride and stirred when the product separated as an oil. To this 500 mL of ethyl acetate was added and stirred again until all the oily product dissolved. The organic layer was transferred to a separatory funnel and washed successively with 500 mL of 0.2 M HCl (3 times), 500 mL 5% sodium bicarbonate solution, and 500 mL of de-ionized water. It was then evaporated to dryness and the residue was stirred with 110 mL of hexane using overhead stirrer. The product solidified into an white powder. Product was isolated by filtration and washed with hexane and dried in a vacuum oven at 40° C. It was characterized using $^1$H NMR, hplc and elemental analysis.

Example 2: Preparation of 3,5-Diiodotyrosine Ethyl Ester Diamide With Adipic Acid ($I_2$TE-AA-$I_2$TE)

Using the above procedure and replacing TE.HCl with $I_2$TE.HCl, the corresponding iodinated monomer $I_2$TE_AA_$I_2$TE was also prepared.

Example 3: Polymerization of TE-AA-TE

Into a 250 mL round-bottomed flask equipped with an overhead stirrer, and syringe pump were added TE-AA-TE (10 g, 19 mmol), 40 mL of methylene chloride, and 5.9 ml (74 mmol) of pyridine. To the flask was then added 2.02 g of triphosgene (20.4 mmol of phosgene) dissolved in 6 mL of methylene chloride using a syringe pump over a 2 h period. The reaction mixture was stirred for 15 min and then stirred with 50 mL de-ionized water for 10 m. After allowing the layers to separate, the top aqueous layer was separated and discarded. The washings were repeated with two additional 50 mL portions of de-ionized water. The reaction mixture was then precipitated with 70 mL of 2-propanol in a laboratory blender. Repeated grinding with 2-propanol hardened the oily precipitate that formed initially.

GPC analysis of the polymer showed a Mw of 99,000 Kda with polydispersity of 1.55. DSC showed a glass transition temperature (Tg) of 81° C.

Example 4: Preparation of SE-Adipic Acid-SE Diamide (SE-AA-SE)

Into a 500 mL round bottomed flask equipped with a mechanical stirrer, and a thermometer are added serine (SE) (13.3 g, 0.10 mol), adipic acid (7.16 g, 0.049 mol), hydroxybenzotriazole (1.35 g, 0.010 mol) and 100 mL of tetrahydrofuran (THF). The flask is maintained under a positive pressure of nitrogen and cooled to 5° C. using an ice-water bath. To the cooled solution is then added EDCI (23 g, 0.12 mol) and stirred at this temperature for 1 h. The cooling bath is then removed and the reaction mixture is allowed to warm up to room temperature and stirred overnight. The reaction mixture is evaporated to dryness and then stirred with a 150 mL of ethyl acetate and 150 mL of 0.2 M HCl. The contents are then transferred to separatory funnel and the layers are allowed to separate. The bottom aqueous layer is removed and discarded. The organic layer is successively washed with 2×50 mL portions of 0.2 M HCl, 50 mL of 5% NaHCO3 solution, and 50 mL of saturated NaCl solution. It is then dried over MgSO4, and evaporated to dryness. The residue is dried under a stream of nitrogen followed by drying in a vacuum oven at 40° C. for 24 h. The product is characterized by $^1$H NMR, HPLC and elemental analysis.

Example 5: Preparation of Serine Octadecyl Ester (SBzOd)

Since the side chain hydroxyl group of serine interferes with this reaction, serine with hydroxyl group protected as benzyl ether (SBz) is used. Into a 500 mL 3-necked flask equipped with an overhead stirrer, a Dean-stark trap, and a thermometer are added 19.5 g (0.10 mol) SBz, 27 g (0.10 mol) of octadecanol (Od), 21 g (0.11 mol) of 4-toluenesulfonic acid (PTSA) monohydrate, and 300 mL of heptane. The contents of the flask are stirred and heated using a heating mantle until the solvents distilled over. Distillation is continued until approximately 3.5 mL water is collected in the side arm of the Dean-Stark trap and further water collection does not occur. The reaction is stopped and allowed to cool to room temperature. The solvent layer is removed by decanting and the residue is stirred with 200 mL hexane and filtered. The residue on the filter funnel is washed with several portions of hexane and dried in a vacuum oven at 40° C.

SBzOd.PTSA obtained as above is stirred with 400 mL of 95% ethanol in a 4 L beaker using an overhead stirrer for 1 h. To this is added with stirring 44 mL of 5 M potassium carbonate solution (0.22 mol of $K_2CO_3$). After stirring for 30 min, 1 L of deionized water is added and stirred vigorously to disperse the solid and then filtered using fritted glass funnel. The residue on the filter funnel is washed with several portions of DI water. The product is dried under a stream of nitrogen followed by drying in a vacuum oven at 40° C. for 24 h. The product (SBzOd) is characterized by $^1$H NMR, HPLC and elemental analysis.

Example 6: Preparation of SBzOd-Adipic Acid-SBzOd Diamide (SBzOd-AA-SBzOd)

Into a 250 mL round bottomed flask equipped with a mechanical stirrer, and a thermometer are added SBzOd (10.5 g, 20 mmol), adipic acid (1.43 g, 9.8 mmol), hydroxybenzotriazole (0.27 g, 2.0 mol) and 100 mL of tetrahydrofuran (THF). The flask is maintained under a positive pressure of nitrogen and cooled to 5° C. using ice-water bath. To the cooled solution is then added EDCI (14.8 g, 0.077 mol) and stirred at this temperature for 1 h. The cooling bath is then removed and the reaction mixture is allowed to warm up to room temperature and stirred overnight. To the reaction mixture is then added 300 mL of 0.2 M HCl, stirred for 5 min and then allowed to stand until the layers separated. The aqueous layer is removed and discarded. The organic layer is further washed with 2×100 mL portions of 0.2 M HCl followed by 100 ml 5% NaHCO3 solution and 100 mL of DI water. The product is isolated by filtration and washed with water. The product is dried under a stream of nitrogen followed by drying in a vacuum oven at 40° C. for 24 h. The product is characterized by $^1$H NMR, HPLC, and elemental analysis.

Ex. 7: Deprotection of SZbOd-AA-SZbOd to Obtain SOd-AA-SOd by Hydrogenation

A parr shaker is used for this reaction. In the Parr shaker bottle 20 g (20 mmol) of SZbOd-AA-SZbOd, 100 mL of DMF, and 1 g of Raney-Nickel are added. The bottle is clamped to the Parr generator and maintained under 60 psi of hydrogen. The bottle is shaken for 2 h. The catalyst is removed by filtration and the filtrate is added to 500 mL DI water with vigorous stirring. The layers are allowed to separate and the aqueous layer is removed and discarded. The organic layer is further washed with 200 mL portions of water until the product precipitates as a white solid which is isolated by filtration and dried in a vacuum oven at 40° C. for 24 h and characterized by 1H NMR and elemental analysis.

Example 8: Polymerization of SOd-AA-SOd by Phosgenation

In a 500 mL 4-necked flask with overhead stirrer are placed 10 g (10 mmol) of SOd-AA-SOd, 100 mL of dry methylene chloride and 3.7 g (47 mmol) of pyridine and stirred for 15 m. In a 20 mL sample bottle 1.1 g of triphosgene (11 meq of phosgene) is dissolved in 8 mL of dry methylene chloride and added to the reaction flask over 2 hours using a syringe pump. The reaction mixture is stirred for 15 minutes and then stirred with 100 mL of water. Layers are allowed to separate and the top aqueous layer is removed and discarded. After 2 additional washes with water, the reaction mixture is precipitated with 150 mL of 2-propanol in a beaker using an overhead stirrer. The product obtained is ground with 50 mL of IPA in a laboratory blender. The product obtained is transferred to a PTFE dish and dried under vacuum for 24 hours at 50° C. The polymer is characterized by GPC, $^1$H NMR spectroscopy, and DSC.

Example 9: Preparation of ThyE-Adipic Acid-ThyE Diamide (ThyE-AA-ThyE)

Into a 500 mL round bottomed flask equipped with a mechanical stirrer, and a thermometer are added thyronine (ThyE) (15.4 g, mol), adipic acid (3.7 g, 0.025 mol), hydroxybenzotriazole (0.80 g, 0.0059 mol) and 150 mL THF. The flask is maintained under a positive pressure on nitrogen and cooled to 5° C. using ice-water bath. To the cooled solution is then added EDCI (14.8 g, 0.077 mol), after which the solution is stirred at this temperature for 1 h. The cooling bath is then removed and the reaction mixture is allowed to warm up to room temperature and stirred overnight. To the reaction mixture is then added 300 mL of 0.2 M HCl, after which the mixture is stirred for 5 min and then allowed to stand. The aqueous layer is removed and discarded. The organic layer is washed with 2×100 mL portions of 0.2 M HCl, followed by washing with 2×100 mL of 5% NaHCO$_3$ solution and 100 mL of DI water. The product is dried under a stream of nitrogen followed by drying in a vacuum oven at 40° C. for 24 h. The product is characterized by $^1$H NMR spectrum and HPLC and elemental analysis.

Example 10: Polymerization of ThyE-AA-ThyE by Phosgenation

In a 500 mL 4-necked flask with overhead stirrer are placed 7.13 g (10.8 mmol) of ThyE-AA-ThyE, 100 mL of methylene chloride and 3.7 g (47 mmol) of pyridine. In a 20 mL sample bottle 0.87 g of triphosgene (11 meq of phosgene) is dissolved in 8 mL of methylene chloride and added to the reaction flask over 2 hours using a syringe pump. The reaction mixture is stirred for 15 minutes and then stirred with 100 mL of water. Layers are allowed separate and the top aqueous layer is removed and discarded. After 2 additional washes with water, the reaction mixture is precipitated with 120 mL of 2-propanol in a beaker using an overhead stirrer. The product is further purified by grinding with IPA in a laboratory blender.

Example 11: Polymerization of ThyE-AA-ThyE by Polyesterification with Adipic Acid In a 20 mL scintillation vial are placed 1.31 g (2.00 mmol) of ThyE-AA-ThyE, 15 mL of methylene chloride and 0.293 g (2.00 mmol) of adipic acid (AA), 0.059 g (0.20 mmol) 4-dimethylaminopyridine-4-toluenesulfonic acid (DPTS), and 0.061 g (0.50 mmol) of 4-dimethylaminopyridine. The contents are stirred with a magnetic stirrer for 30 min and then 0.76 g (6.00 mmol) of N,N'-diisopropylcarbodiimide is added and stirred. The Mw is determined at various intervals and the reaction is allowed to go until the desired MW is reached. The reaction mixture is then precipitated with IPA and purified further by grinding with IPA in a laboratory blender. The product obtained is transferred to a dish and dried in vacuum oven at 40° C. for 24 hours. The polymer is characterized by GPC, $^1$H NMR and DSC.

Example 12: Preparation of TE-PLLA-TE Diamide (TE-PLLA-TE)

Into a 500 mL round bottomed flask equipped with a mechanical stirrer, and a thermometer are added TE (10.7 g, 0.051 mol), PLLA of molecular weight 2000 with both terminus ending with COOH (50 g, 0.025 mol), hydroxybenzotriazole (0.80 g, 0.0059 mol) and 250 mL THF. The flask is maintained under a positive pressure on nitrogen and cooled to 5° C. using ice-water bath. To the cooled solution is then added EDCI (14.8 g, 0.077 mol) and stirred at this temperature for 1 h. The cooling bath is then removed and the reaction mixture is allowed to warm up to room temperature and stirred overnight. To the reaction mixture is then added 500 mL of 0.2 M HCl, which is stirred for 5 min and then allowed to stand. The aqueous layer is removed and discarded. The organic layer is washed with 2×100 mL portions of 0.2 M HCl, followed by washing with 2×100 mL of 5% NaHCO$_3$ solution and 100 mL of DI water. The product is dried under a stream of nitrogen followed by drying in a vacuum oven at 40° C. for 24 h. The product (TE-PLLA-TE) is characterized by $^1$H NMR spectrum, and HPLC, GPC and elemental analysis.

Example 13: Polymerization of TE-PLLA-TE by Phosgenation

In a 500 mL 4-necked flask with overhead stirrer are placed 24 g (10.0 mmol) of TE-PLLA-TE, 200 mL methylene chloride and 3.7 g (47 mmol) of pyridine. In a 20 mL sample bottle 0.87 g of triphosgene (11 meq phosgene) is dissolved in 8 mL of methylene chloride and added to the reaction flask over 2 hours using a syringe pump. The reaction mixture is stirred for 15 minutes and then stirred with 200 mL water. Layers are allowed to separate and the top aqueous layer is removed and discarded. After two additional washes with water, the reaction mixture is precipitated with 120 mL of 2-propanol (IPA) in a beaker using an overhead stirrer. The product is further purified by grinding with IPA in a laboratory blender. The product is characterized by $^1$H NMR spectrum, and HPLC, GPC and DSC.

Example 14: Polymerization of TE-PLLA-TE by Polyesterification with Adipic Acid In a 50 mL round-bottomed flask are placed 4.8 g (2.00 mmol) of TE-PLLA-TE, 25 mL methylene chloride and 0.293 g (2.00 mmol) adipic acid (AA), 0.059 g (0.20 mmol) DPTS, and 0.061 g (0.50 mmol) of 4-dimethlyaminopyridine. The contents are stirred with a magnetic stirrer for 30 min and then 0.76 g (6.00 mmol) of N,N'-diisopropylcarbodiimide is added and stirred. The Mw is determined at various intervals and the reaction is allowed to continue until the desired MW is reached. The reaction mixture is then precipitated with IPA and purified further by grinding with IPA in a laboratory blender. The product obtained is transferred to a dish and dried in vacuum oven at 40° C. for 24 hours. The polymer is characterized by GPC, $^1$H NMR and DSC.

Example 15: Preparation of Ztyr-PLLA-Ztyr

Into a 250 mL 3-necked flask are added 7.9 g (25 mmol) Z-tyrosine (Ztyr), 20 g (12 mmol) of PLLA2000-diol, 0.47 g (2.5 mmol) PTSA and 250 mL heptane. The flask is equipped with a Dean-stark trap, an overhead stirrer, and a thermometer. The contents of the flask are stirred and heated using a heating mantle for 4 hrs. when approximately 0.7 mL water collected in the Dean-Stark trap. Further reflux did not produce additional water. The solvent is decanted and the residue is dissolved in 30 mL THF. The solution is stirred with 100 mL 5% $NaHCO_3$ solution. The aqueous layer is removed and discarded. The residue is washed with two 50 mL portions of 5% $NaHCO_3$ solution. This is stirred with 50 mL of DI water and then dried under vacuum. The product is characterized by $^1$H NMR and HPLC.

Example 16: Polymerization of Ztyr-PLLA-Ztyr by Phosgenation

In a 500 mL 4-necked flask with overhead stirrer are placed 26 g (10.0 mmol) of Ztyr-PLLA-Ztyr, 200 mL of methylene chloride and 3.7 g (47 mmol) pyridine. In a 20 mL sample bottle 0.87 g of triphosgene (11 meq of phosgene) is dissolved in 8 mL of methylene chloride and added to the reaction flask over 2 hours using a syringe pump. The reaction mixture is stirred for 15 minutes and then stirred with 200 mL of water. Layers are allowed separate and the top aqueous layer is removed and discarded. After 2 additional washes with water, the reaction mixture is precipitated with 120 mL of 2-propanol (IPA) in a beaker using an overhead stirrer. The product is further purified by grinding with IPA in a laboratory blender. The product is characterized by $^1$H NMR, HPLC, GPC and DSC.

Example 17: Polymerization of Ztyr-PLLA-Ztyr by Polyesterification with Adipic Acid In a 50 mL round-bottomed flask are placed 5.2 g (2.00 mmol) Ztyr-PLLA-Ztyr, 25 mL methylene chloride and 0.293 g (2.00 mmol) adipic acid (AA), 0.059 g (0.20 mmol) DPTS, and 0.061 g (0.50 mmol) 4-dimethlyaminopyridine. The contents are stirred with a magnetic stirrer for 30 min and then 0.76 g (6.00 mmol) of N, N'-diisopropylcarbodiimide is added and stirred. The Mw is determined at various intervals and the reaction is allowed to continue until the desired MW is reached. The reaction mixture is then precipitated with IPA and purified further by grinding with IPA in a laboratory blender. The product obtained is transferred to a dish and dried in vacuum oven at 40° C. for 24 h. The polymer is characterized by GPC, $^1$H NMR and DSC.

Example 18: Preparation of TBz-Adipic Acid-TBz Diamide (TBz-AA-TBz)

Into a 500 mL round bottomed flask equipped with a mechanical stirrer, and a thermometer are added tyrosine benzyl ester (TBz) (13.8 g, 0.051 mol), Adipic acid (3.7 g, 0.025 mol), hydroxybenzotriazole (0.80 g, 0.0059 mol) and 150 mL THF. The flask is maintained under a positive pressure on nitrogen and cooled to 5° C. using ice-water bath. To the cooled solution is then added EDCI (14.8 g, 0.077 mol) and stirred at this temperature for 1 h. The cooling bath is then removed and the reaction mixture is allowed to warm up to room temperature and stirred overnight. To the reaction mixture is then added 300 mL of 0.2 M HCl, stirred for 5 min and then allowed to stand. The aqueous layer is removed and discarded. The organic layer is washed 2 portions of 100 mL of 0.2 M HCl and the aqueous layer is discarded each time. It is further washed with 2×100 mL of 5% $NaHCO_3$ solution and 50 mL of DI water. The product is dried under a stream of nitrogen followed by drying in a vacuum oven at 40° C. for 24 h. The product is characterized by $^1$H NMR and HPLC.

Example 19: Polymerization of TBz-AA-TBz by Phosgenation

In a 500 mL 4-necked flask with overhead stirrer are placed 9.8 g (15 mmol) of TBz-AA-TBz, 100 mL of methylene chloride and 3.7 g (47 mmol) pyridine. In a 20 mL sample bottle 1.57 g triphosgene (16 meq phosgene) is dissolved in 8 mL methylene chloride and added to the reaction flask over 2 hours using a syringe pump. The reaction mixture is stirred for 15 minutes and then stirred with 100 mL water. Layers are allowed to separate and the top aqueous layer is removed and discarded. After two additional washes with water, the reaction mixture is precipitated with 120 mL 2-propanol in a beaker using an overhead stirrer. The product obtained is transferred to a PTFE dish, dried under vacuum for 24 hrs. at 50° C., and characterized by GPC, $^1$H NMR and DSC.

Ex. 20: Polyesterification of TBz-AA-TBz with Adipic Acid (Poly(TBz-AA-TBz Adipate)

In a 20 mL scintillation vial are placed 1.3 g (2.00 mmol) of TBz-AA-TBz, 15 mL of methylene chloride, 0.293 g (2.00 mmol) of adipic acid (AA), 0.059 g (0.20 mmol) DPTS and 0.061 g (0.50 mmol) 4-dimethlyaminopyridine. The contents are stirred with a magnetic stirrer for 30 min and then 0.76 g (6.00 mmol) N,N'-diisopropylcarbodiimide is added and stirred. The Mw is determined at various intervals and the reaction is allowed to continue until the desired MW is reached. The reaction mixture is then precipitated with IPA and purified further by grinding with IPA in laboratory blender. The product obtained is transferred to a dish and dried in a vacuum oven at 40° C. for 24 hrs. The polymer is characterized by GPC, $^1$H NMR and DSC.

Example 21: Deprotection of Poly(TBz-AA-TBz Carbonate)

In 250 mL Parr shaker bottle 10 g of poly(TBz-AA-TBZ carbonate) is stirred with 100 mL DMF. To this 1 g of palladium on barium sulfate (Pd/$BaSO_4$) is added and the bottle is clamped to the par shaker and hydrogen gas pressure of 60 psi is maintained. It is agitated for 4 h and then the contents of the bottle are filtered using a fine fritted glass funnel. The filtrate is precipitated with 500 mL of DI water with vigorous stirring and the precipitate obtained is stirred with 3 100 mL portions of DI water. The product is isolated by filtration and washed with water. The product is dried in a vacuum oven at 40° C. for 24 h. The polymer is characterized by GPC, $^1$H NMR and DSC.

Example 22: Deprotection of Poly(TBz-AA-TBz Adipate)

In 250 mL Parr shaker bottle 10 g of poly(TBz-AA-TBZ adipate) is stirred with 100 mL DMF. To this 1 g of palladium on barium sulfate (Pd/BaSO$_4$) is added and the bottle is clamped to the par shaker and hydrogen gas pressure of 60 psi is maintained. It is agitated for 4 h and then the contents of the bottle are filtered using a fine fritted glass funnel. The filtrate is precipitated with 500 mL of DI water with vigorous stirring and the precipitate obtained is stirred with 3 100 mL portions of DI water. The product is isolated by filtration and washed with water. The product is dried in a vacuum oven at 40° C. for 24 h. The polymer is characterized by GPC, $^1$H NMR and DSC.

Example 23: Preparation of TtBu-Adipic Acid-TtBu Diamide (TtBu-AA-TtBu)

Into a 500 mL round bottomed flask equipped with a mechanical stirrer, and a thermometer are added tyrosine t-butyl ester (TtBu) (12.9 g, 0.051 mol), adipic acid (3.7 g, 0.025 mol), hydroxybenzotriazole (0.80 g, 0.0059 mol) and 150 mL THF. The flask is maintained under a positive pressure on nitrogen and cooled to 5° C. using an ice-water bath. To the cooled solution is then added EDCI (14.8 g, 0.077 mol) and the solution is stirred at this temperature for 1 h. The cooling bath is then removed and the reaction mixture is allowed to warm up to room temperature and stirred overnight. To the reaction mixture is then added 300 mL of 0.2 M HCl, stirred for 5 min and the mixture is then allowed to stand. The aqueous layer is removed and discarded. The organic layer is washed 2 portions of 100 mL of 0.2 M HCl and the aqueous layer is discarded each time. It is further washed with 2×100 mL of 5% NaHCO$_3$ solution and 50 mL of DI water. The product is dried under a stream of nitrogen followed by drying in a vacuum oven at 40° C. for 24 h. The product is characterized by $^1$H NMR and HPLC.

Example 24: Polymerization of TtBu-AA-TtBu by Phosgenation

In a 500 mL 4-necked flask with overhead stirrer are placed 8.8 g (15 mmol) of TtBu-AA-TtBu, 100 mL of methylene chloride and 3.7 g (47 mmol) pyridine. In a 20 mL sample bottle 1.57 g of triphosgene (16 meq phosgene) is dissolved in 8 mL of methylene chloride and added to the reaction flask over 2 hours using a syringe pump. The reaction mixture is stirred for 15 minutes and then stirred with 100 mL water. Layers are allowed separate and the top aqueous layer is removed and discarded. After two additional washes with water, the reaction mixture is precipitated with 120 mL 2-propanol in a beaker using an overhead stirrer. The product obtained was transferred to a PTFE dish and dried under vacuum for 24 hours at 50° C. The product is characterized by GPC, $^1$H NMR and DSC.

Example 25: Polyesterification of TtBu-AA-TtBu with Adipic Acid (Poly(TtBu-AA-TtBu Adipate)

In a 20 mL scintillation vial are placed 1.3 g (2.00 mmol) of TtBu-AA-TtBu, 15 mL of methylene chloride, 0.293 g (2.00 mmol) of adipic acid (AA), 0.059 g (0.20 mmol) DPTS, and 0.061 g (0.50 mmol) 4-dimethlyaminopyridine. The contents are stirred with a magnetic stirrer for 30 min and then 0.76 g (6.00 mmol) N,N'-diisopropylcarbodiimide is added and stirred. The Mw is determined at various intervals and the reaction is allowed to continue until the desired MW is reached. The reaction mixture is then precipitated with IPA and purified further by grinding with IPA in laboratory blender. The product obtained is transferred to a dish and dried in vacuum oven at 40° C. for 24 h. The polymer is characterized by GPC, $^1$H NMR and DSC.

Example 26: Deprotection of Poly(TtBu-AA-TtBu Carbonate)

In 50 mL round bottomed flask 5 g of poly(TtTbu-AA-TtTBu carbonate) is stirred with 26 mL methylene chloride. To this 8 mL trifluroacetic acid is added and stirred at ambient temperature for 16 h. The reaction mixture is then precipitated by adding it to 100 mL of IPA. The precipitate obtained is ground with IPA in a laboratory blender to further purify it. The product is isolated by filtration and washed with IPA. The product is dried in a vacuum oven at 40° C. for 24 h., and characterized by GPC, $^1$H NMR and DSC.

Example 27: Deprotection of Poly(TBz-AA-TBz Adipate)

In a 50 mL round bottomed flask 5 g of poly(TBz-AA-TBz adipate) is stirred with 26 mL methylene chloride. To this 8 mL of trifluoroacetic acid is added and stirred at ambient temperature for 16 h. The reaction mixture is then precipitated by adding it to 100 mL of IPA. The precipitate obtained is ground with IPA in a laboratory blender to further purify it. The product is isolated by filtration and washed with IPA. The product is dried in a vacuum oven at 40° C. for 24 h., and characterized by GPC, $^1$H NMR and DSC.

Example 28: Preparation of Threonine Octadecyl Ester (ThBzOd)

Because the side chain hydroxyl group of threonine (Th) interferes with this reaction, threonine with the hydroxyl group protected as benzyl ether (ThBz) is used. Into a 500 mL 3-necked flask equipped with an overhead stirrer, a Dean-stark trap, and a thermometer are added 13.3 g (0.10 mol) ThBz, 27 g (0.10 mol) octadecanol (Od), 21 g (0.11 mol) PTSA monohydrate, and 300 mL heptane. The contents of the flask are stirred and heated using a heating mantle until the solvents distilled. Distillation is continued until approximately 3.5 mL of water is collected in the side arm of the Dean-Stark trap and further water collection does not occur. The reaction is stopped and allowed to cool to room temperature. The solvent layer is removed by decanting and the residue is stirred with 200 mL of hexane and filtered. The residue on the filter funnel is washed with several portions of hexane and dried in a vacuum oven at 40° C.

Example 29: Preparation of ThE-Adipic Acid-ThE Diamide (ThE-AA-ThE)

Into a 500 mL round bottomed flask equipped with a mechanical stirrer, and a thermometer are added ThE (14.7 g, 0.10 mol), Adipic acid (7.16 g, 0.049 mol), hydroxylbenzotriazole (1.35 g, 0.010 mol) and 100 mL THF. The flask is maintained under a positive pressure of nitrogen and cooled to 5° C. using an ice-water bath. To the cooled solution is then added EDCI (23 g, 0.12 mol) and the solution is stirred at this temperature for 1 h. The cooling bath is then removed and the reaction mixture is allowed to warm up to room temperature and stirred overnight. The reaction mixture is evaporated to dryness and then stirred with a 150 mL of ethyl acetate and 150 mL of 0.2 M HCl. The contents are then transferred to separatory funnel and the layers are allowed to separate. The bottom aqueous layer is removed and discarded. The organic layer is successively washed with 2 50 mL portions of 02 M HCl, 50 mL of 5% NaHCO3 solution, and 50 mL of NaCl solution. It is then dried over MgSO4, and evaporated to dryness. The residue is dried under a stream of nitrogen followed by drying in a vacuum oven at 40° C. for 24 h. The product is characterized by $^1$H NMR. HPLC and elemental analysis.

Example 30: Polymerization of ThE-AA-ThE by polyesterification with adipic acid In a 50 mL round bottom flask are placed 2.5 g (4.0 mmol) ThE-AA-ThE, 15 mL methylene chloride, 0.585 g (4.00 mmol) adipic acid (AA), 0.12 g (0.40 mmol) DPTS and 0.061 g (0.50 mmol) 4-dimethlyaminopyridine. The contents are stirred with a magnetic stirrer for 30 min and then 1.51 g (12.0 mmol) N,N'-diisopropylcarbodiimide is added and stirred. After about an hour the reaction mixture becomes a gel and stirring is stopped. Mw is measured by GPC and the reaction is continued until the desired MW is obtained. The gel is added with stirring to 100 mL IPA in a beaker. A swollen gel is obtained that is isolated by filtration on a fritted glass funnel. It is washed on the filter funnel with 3×20 mL portions of IPA. The product obtained is transferred to a dish. dried in a vacuum oven at 40° C. for 24 h., and characterized by GPC, DSC, and $^1$H NMR.

Example 31: Polyesterification of ThE-AA-ThE with 1,12-Dodecanedioic Acid

In a 50 mL round-bottomed flask are placed 2.5 g (4.0 mmol) of ThE-AA-ThE, 25 mL of methylene chloride, 0.92 g (4.0 mmol) of 1,12-dodecanedioic acid (DD), 0.74 g (2.5 mmol) DPTS and 0.061 g (0.50 mmol) 4-dimethylaminopyridine. The contents are stirred with a magnetic stirrer for 30 min and then 1.51 g (12 mmol) N,N'-diisopropylcarbodiimide is added and stirred. After about an hour the reaction MW is determined by GPC and the reaction is continued until the desired MW is reached. The product is precipitated by adding it 100 mL of IPA, followed by grinding the polymer with IPA in a laboratory blender. The product is dried in vacuum oven at 40° C. for 24 h.

Example 32: Preparation of Threonine Octadecyl Ester (ThBzOd)

Since the side chain hydroxyl group of threonine interferes with this reaction, threonine with hydroxyl group protected as benzyl ether (ThBz) is used. Into a 500 mL 3-necked flask equipped with an overhead stirrer, a Dean-stark trap, and a thermometer are added 13.3 g (0.10 mol) ThBz, 27 g (0.10 mol) octadecanol (Od), 21 g (0.11 mol) PTSA monohydrate, and 300 mL heptane. The contents of the flask are stirred and heated using a heating mantle until the solvents distilled. Distillation is continued until approximately 3.5 mL of water is collected in the side arm of the Dean-Stark trap and further water collection does not occur. The reaction is stopped and allowed to cool to room temperature. The solvent layer is removed by decanting and the residue is stirred with 200 mL of hexane and filtered. The residue on the filter funnel is washed with several portions of hexane and dried in a vacuum oven at 40° C.

BzThOd.PTSA obtained above is stirred with 400 mL 95% ethanol in a 4 L beaker using an overhead stirrer for 1 h. To this is added with stirring 44 mL of 5 M potassium carbonate solution (0.22 mol of $K_2CO_3$). After stirring for 30 min, 1 L of deionized water is added and stirred vigorously to disperse the solid and then filtered using fritted glass funnel. The residue on the filter is washed with several portions of DI water. The product is dried under a stream of nitrogen followed by drying in a vacuum oven at 40° C. for 24 h. The product is characterized by $^1$H NMR, HPLC and elemental analysis.

Ex. 33: Preparation of ThBzOd-Adipic Acid-ThBzOd Diamide (ThBzOd-AA-ThBzOd)

Into a 250 mL round bottomed flask equipped with a mechanical stirrer, and a thermometer are added ThBzOd (9.23 g, 20 mmol), Adipic acid (1.25 g, 9.8 mmol), hydroxylbenzotriazole (0.27 g, 2.0 mol) and 100 mL THF. The flask is maintained under a positive pressure on nitrogen and cooled to 5° C. using ice-water bath. To the cooled solution is then added EDCI (14.8 g, 0.077 mol) and stirred at this temperature for 1 h. The cooling bath is then removed and the reaction mixture is allowed to warm up to room temperature and stirred overnight. To the reaction mixture is then added 300 mL of 0.2 M HCl, stirred for 5 min and then allowed to stand until the layers separated. The aqueous layer is removed and discarded. The organic layer is further washed with two 100 mL portions of 0.2 M HCl followed by 100 ml 5% NaHCO3 solution and 100 mL of DI water. The product is isolated by filtration and washed with water. The product is dried under a stream of nitrogen followed by drying in a vacuum oven at 40° C. for 24 h. The product is characterized by $^1$H NMR, HPLC and elemental analysis.

Example 34: Deprotection of ThZbOd-AA-ThZbOd by Hydrogenation to Obtain ThOd-AA-ThOd A Parr shaker is used for this reaction. In the Parr shaker bottle 20.7 g (20 mmol) of ThZbOd-AA-ThZbOd, 100 mL of DMF, and 1 g of Raney-Nickel are added. The bottle is clamped to the Parr generator and maintained at 60 psi of hydrogen. The bottle is shaken for 2 h. The catalyst is removed by filtration and the filtrate is added to 500 mL of DI water with vigorous stirring. The layers are allowed to separate and the aqueous layer is removed and discarded. The organic layer is further washed with 200 mL portions of water until the product precipitates as white solid isolated filtration dried in vacuum oven at 40° C. for 24 h and characterized by 1H NMR and elemental analysis.

Example 35: Polymerization of ThOd-AA-ThOd by Phosgenation

In a 500 mL 4-necked flask with overhead stirrer are placed 8.53 g (10 mmol) of ThOd-AA-ThOd, 100 mL of dry methylene chloride and 3.7 g (47 mmol) of pyridine and stirred for 15 m. In a 20 mL sample bottle 1.1 g of triphosgene (11 meq of phosgene) is dissolved in 8 mL of dry methylene chloride and added to the reaction flask over 2 hours using a syringe pump. The reaction mixture is stirred for 15 minutes (note: additional triphosgene may be needed to get desired MW) and then stirred with 100 mL of water. Layers are allowed separate and the top aqueous layer is removed and discarded. After 2 additional washes with water, the reaction mixture is precipitated with 150 mL IPA in a beaker using an overhead stirrer. The product obtained is ground with 50 mL of IPA in a laboratory blender. The product obtained is transferred to a PTFE dish and dried under vacuum for 24 hours at 50° C. The polymer is characterized by GPC, $^1$H NMR and DSC.

Example 36: Polyesterification of ThOd-AA-ThOd with 1,12-Dodecane Diioic Acid

In a 50 mL round-bottomed flask are placed 2.13 g (2.50 mmol) ThOd-AA-ThOd, 25 mL of methylene chloride and 0.576 g (2.50 mmol) of 1,12-dodecanedioic acid (DD), 0.44 g (1.5 mmol) DPTS and 0.061 g (0.50 mmol) of 4-dimethlyaminopyridine. The contents are stirred with a magnetic stirrer for 30 min and then 0.95 g (7.5 mmol) N,N'-diisopropylcarbodiimide is added and stirred. The molecular weight is periodically checked by GPC and when the desired MW is reached the reaction is stopped. The product is precipitated by adding it 100 mL of IPA, followed by grinding the precipitate with IPA in a laboratory blender. The polymer is dried in a stream of nitrogen followed by drying in vacuum oven at 40° C. The polymer is characterized by GPC, $^1$H NMR and DSC.

Example 37: Preparation of XTh-PrD-XTh

Into a 250 mL 3-necked flask were added 6.3 g (25 mmol) of threonine that is N-protected with acetyl group and O-protected as benzyl ether (XTh), 0.91 g (12 mmol) of 1,3-propanediol, 0.48 g (2.5 mmol) PTSA and 150 mL heptane. The flask is equipped with a Dean-stark trap, an overhead stirrer, and a thermometer. The contents of the flask were stirred and heated using a heating mantle for 4 h when approximately 0.4 mL of water collected in the Dean-Stark trap. Further reflux did not produce additional water. The reaction mixture is allowed to cool when the product became a semi-solid. The solvent is decanted out and the residue is stirred with 30 mL of THF when most of it dissolved leaving behind a small amount of insoluble residue, which is removed by filtration. The filtrate is stirred with 100 mL of 5% $NaHCO_3$ solution, when an oil layer separated. This oil is stirred with two 50 mL portions of 5% $NaHCO_3$ solution when a semisolid resulted. This is stirred with 50 mL of DI water and then dried under vacuum. The product obtained is a semisolid and is characterized by its $^1$H NMR spectrum and HPLC, which showed several impurities other than the product, starting material and the mono addition adduct. The product is purified by flash chromatography on a silica gel column using a gradient using suitable mixtures of ethyl acetate-heptane as the eluent. The purified material is characterized by LC/MS (negative ion mode), $^1$H NMR and TLC.

Ex. 38: Deprotection of XTh-PrD-XTh to Obtain AcTh-PrD-ACTh by Hydrogenation

A Parr shaker is used for this reaction. In the Parr shaker bottle 10.9 g (20 mmol) XTh-PrD-XTh, 100 of DMF, and 1 g of Raney-Nickel are added. The bottle is clamped to the Parr generator and maintained at 60 psi of hydrogen. The bottle is shaken for 2 h. The catalyst is removed by filtration and the filtrate is added to 500 mL of DI water with vigorous stirring. The layers are allowed to separate and the aqueous layer is removed and discarded. The organic layer is further stirred vigorously with 200 mL portions of water until the product precipitates as a white solid that is isolated by filtration, dried in vacuum oven at 40° C. for 24 h and characterized by $^1$H NMR and elemental analysis.

Example 39: Polymerization of AcTh-PrD-ACTh by Phosgenation

In a 500 mL 4-necked flask with overhead stirrer are placed 8.53 g (10 mmol) of AcTh-PrD-ACTh, 100 mL dry methylene chloride and 3.7 g (47 mmol) of pyridine and stirred for 15 m. In a 20 mL sample bottle 1.1 g of triphosgene (11 meq of phosgene) is dissolved in 8 mL of dry methylene chloride and added to the reaction flask over 2 hours using a syringe pump. The reaction mixture is stirred for 15 minutes (note: additional triphosgene may be needed to get desired MW) and then stirred with 100 mL of water. Layers are allowed to separate and the top aqueous layer is removed and discarded. After two additional washes with water, the reaction mixture is precipitated with 150 mL IPA in a beaker using an overhead stirrer. The product obtained is ground with 50 mL IPA in a laboratory blender. The product obtained is transferred to a PTFE dish and dried under vacuum for 24 h. at 50° C. The polymer is characterized by GPC, $^1$H NMR and DSC.

Example 40: Polyesterification of AcTh-PrD-ACTh with 1,12-Dodecanedioic Acid

In a 50 mL round-bottomed flask are placed 2.2 g (4.0 mmol) AcTh-PrD-ACTh, 25 mL of methylene chloride, 0.92 g (4.0 mmol) of 1,12-dodecanedioic acid (DD), 0.74 g (2.5 mmol) DPTS and 0.061 g (0.50 mmol) of 4-dimethlyaminopyridine. The contents are stirred with a magnetic stirrer for 30 min and then 1.51 g (12 mmol) N,N'-diisopropylcarbodiimide is added and stirred. After about an hour the reaction MW is determined by GPC and the reaction is continued until the desired MW is reached. The product is precipitated by adding 100 mL of IPA, followed by grinding the polymer with IPA in a laboratory blender. The product is dried in vacuum oven at 40° C. for 24 h.

Example 41: Preparation of AcTyr-PrD-AcTyr

Into a 250 mL 3-necked flask are added 5.6 g (25 mmol) of N-acetyl-tyrosine (AcTyr), 0.91 g (12 mmol) of 1,3-propanediol, 0.47 g (2.5 mmol) PTSA and 150 mL of heptane. The flask is equipped with a Dean-stark trap, an overhead stirrer, and a thermometer. The contents of the flask are stirred and heated using a heating mantle until water collection in the side arm of the Dean-Stark trap. The reaction mixture is allowed to cool and the solvent is decanted out. The residue is dissolved in THF. The filtrate is stirred with 100 mL of 5% $NaHCO_3$ solution and the oil that separates is stirred with two 50 mL portions of 5% $NaHCO_3$ solution. The residue obtained is stirred with 50 mL of DI water and then dried under vacuum. The product obtained is characterized by $^1$H NMR and HPLC. The product is purified by flash chromatography on a silica gel column using a gradient with 40:60 to 50:50 ethyl acetate-heptane as the eluent. which is characterized by LC/MS (negative ion mode), $^1$H NMR and TLC.

Example 42: Polymerization of AcTyr-PrD-AcTyr by Phosgenation

In a 500 mL 4-necked flask with overhead stirrer are placed 3.1 g (6 mmol) of AcTyr-PrD-AcTyr, 25 mL of methylene chloride and 1.9 g (24 mmol) of pyridine. A clear solution formed on stirring. In a 20 mL sample bottle 0.61 g of triphosgene (6.2 meq of phosgene) is dissolved in 10 mL of methylene chloride and added to the reaction flask over 2 hours using the syringe pump. The reaction mixture is stirred for 15 minutes and then stirred with 50 mL of water. Layers are allowed to separate and the top aqueous layer is removed and discarded. After 2 additional washes with water, the reaction mixture is precipitated with 30 mL of 2-propanol in a beaker using a magnetic stirrer. Allowed to settle for 1 hour and then the supernatant is decanted off and discarded. The precipitate is stirred with 20 mL of IPA in the beaker twice. The polymer is obtained as a wet mass. The product is transferred to a PTFE dish and dried in a vacuum oven for 24 h at 50° C. The polymer is characterized by GPC, $^1$H NMR and DSC.

Example 43: Preparation of I2TE-AA-I2TE

TE-AA-TE (5 g, 9 mmol) was dissolved in 50 mL of ethanol 7 mL of pyridine in a 250 mL Erlenmeyer flask. To this was added with vigorous stirring 19.4 mL of 2M KICl$_2$ solution (39 mmol) over 10 min. The contents were stirred for additional 2 h. To the reaction mixture was added 200 mL of DI water and then the precipitate was isolated by filtration and washed with water in the filer funnel. The product was dried in vacuum oven at 40° C. or 24 h. The product was characterized by $^1$H NMR and HPLC.

Example 44: Preparation of I2TOd-AA-I2TOd

TOd-AA-TOd (4.9 g, 5 mmol) was dissolved in 50 mL of ethanol 3.5 mL (44 mmol) of pyridine in a 250 mL Erlenmeyer flask. To this was added with vigorous stirring 10.3 mL of 2M KICl$_2$ solution (21 mmol) over 10 min. The contents were stirred for additional 2 h. To the reaction mixture was added 200 mL of DI water and then the precipitate was isolated by filtration and washed with water in the filter funnel. The product was dried in vacuum oven at 40° C. for 24 h. The product was characterized by $^1$H NMR and HPLC.

Example 45: Preparation of I2AcTyr-PrD-I2AcTyr

AcTyr-PrD-AcTyr (5.1 g, 10 mmol) is dissolved in 50 mL of ethanol and 8 mL (21 mmol) pyridine in a 250 mL Erlenmeyer flask. To this is added with vigorous stirring 19.4 mL 2M KICl$_2$ solution (39 mmol) over 10 min. The contents are stirred for additional 2 h. To the reaction mixture is added 200 mL DI water and then the precipitate is isolated by filtration and washed with water in the filer funnel. The product is dried in vacuum oven at 40° C. for 24 h. The product is characterized by $^1$H NMR and HPLC.

It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

What is claimed is:

1. A monomer compound having the structure of formula:

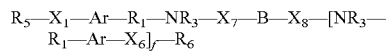

wherein f is 0 or 1;
$X_1$ and $X_6$ are independently selected from the group consisting of O, S and $NR_3$, wherein $R_3$ is selected from the group consisting of hydrogen and alkyl groups containing from one to six carbon atoms;
$X_7$ and $X_8$ are independently selected from the group consisting of —(C=O)—O—, —(C=O)—S—, and —(C=O)—;
wherein Ar at each occurrence is independently selected from the group consisting of phenylene,

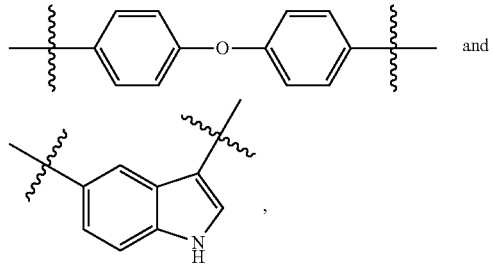

and optionally substituted with from one to four substituents per Ar group independently selected from the group consisting of halogen, halomethyl, halomethoxy, methyl, thiomethyl, nitro, sulfoxide and sulfonyl;
wherein $R_1$ at each occurrence is independently selected from the group consisting of optionally substituted $C_1$-$C_{10}$ alkylene, $C_1$-$C_{10}$ heteroalkylene, $C_2$-$C_{10}$ alkenylene and $C_2$-$C_{10}$ hetero-alkenylene, wherein at least one occurrence of $R_1$ further comprises a pendant carboxylate ester group containing 3 to 30 carbon atoms in addition to the number of carbon atoms defined for said $R_1$ group;
$R_3$ is hydrogen;
$R_5$ and $R_6$ are independently selected from the group consisting of hydrogen and alkyl groups containing from one to six carbon atoms; and
B is selected from the group consisting of optionally substituted alkylene groups, optionally substituted heteroalkylene groups, optionally substituted alkenylene groups and optionally substituted heteroalkenylene groups, or B is selected so that the segment —$X_7$—B—$X_8$— is obtained from a starting material $HX_7$—B—$X_8$H, which is selected from a hydroxyl endcapped macromer or a thiol endcapped macromer,
wherein the optional substituents on B are selected from the group consisting of alkyl, alkenyl, cycloalkyl, cycloalkenyl, aryl, heteroaryl, heteroalicyclyl, aralkyl, heteroaralkyl, (heteroalicyclyl)alkyl, hydroxy, alkoxy, aryloxy, mercapto, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino and di-substituted amino.

2. The monomer of claim 1, wherein Ar, $R_1$, $R_5$, $X_1$, $X_6$ and $R_6$ are selected so that the segment $R_5$—$X_1$—Ar—$R_1$—

NR$_3$— is obtained from R$_5$—X$_1$—Ar—R$_1$—NH$_2$, and the segment —NR$_3$—R$_1$—Ar—X$_6$—R$_6$ is obtained from NH$_2$—R$_1$—Ar—X$_6$—R$_6$ and at least one of these structures is an amino acid.

3. The monomer of claim 2, wherein Ar, R$_1$, R$_5$, X$_1$, X$_6$ and R$_6$ are selected so that the segment R$_5$—X$_1$—Ar—R$_1$—NR$_3$— is obtained from R$_5$—X$_1$—Ar—R$_1$—NH$_2$, and the segment —NR$_3$—R$_1$—Ar—X$_6$—R$_6$ is obtained from NH$_2$—R$_1$—Ar—X$_6$—R$_6$, and both of these structures are amino acids.

4. The monomer of claim 2, wherein the amino acid is selected from the group consisting tyrosine, thyronine, and hydroxyl-tryptophan.

5. The monomer of claim 1, wherein each X$_1$ and X$_6$ is an oxygen atom.

6. A monomer compound having the structure of formula:

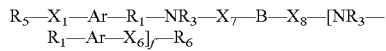

wherein f is 0 or 1;

X$_1$ and X$_6$ are independently selected from the group consisting of O, S and NR$_3$, wherein R$_3$ is selected from the group consisting of hydrogen and alkyl groups containing from one to six carbon atoms;

X$_7$ and X$_8$ are independently selected from the group consisting of —(C=O)—O—, —(C=O)—S—, and —(C=O)—;

wherein Ar at each occurrence is independently selected from the group consisting of phenylene,

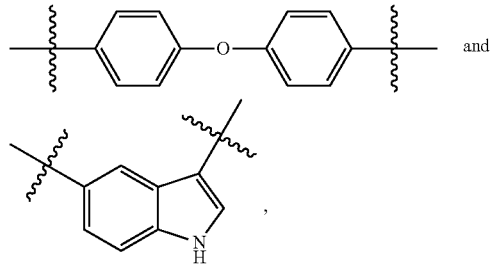

optionally substituted with from one to four substituents per Ar group independently selected from the group consisting of halogen, halomethyl, halomethoxy, methyl, thiomethyl, nitro, sulfoxide and sulfonyl;

wherein R$_1$ at each occurrence is independently selected from the group consisting of optionally substituted C$_1$-C$_{10}$ alkylene, C$_1$-C$_{10}$ heteroalkylene, C$_2$-C$_{10}$ alkenylene and C$_2$-C$_{10}$ hetero-alkenylene, wherein at least one occurrence of R$_1$ further comprises a pendant carboxylate ester group containing 3 to 30 carbon atoms in addition to the number of carbon atoms defined for said R$_1$ group;

R$_3$ is hydrogen;

R$_5$ and R$_6$ are independently selected from the group consisting of hydrogen and alkyl groups containing from one to six carbon atoms; and B is selected from the group consisting of optionally substituted alkylene groups, optionally substituted heteroalkylene groups, optionally substituted alkenylene groups and optionally substituted heteroalkenylene groups, or B is selected so that the segment —X$_7$—B—X$_8$— is obtained from a starting material HX$_7$—B—X$_8$H, which is selected from a hydroxyl endcapped macromer or a thiol endcapped macromer;

wherein when B is optionally substituted heteroalkylene the optional substituents are selected from the group consisting of alkyl, alkenyl, cycloalkyl, cycloalkenyl, aryl, heteroaryl, heteroalicyclyl, aralkyl, heteroaralkyl, (heteroalicyclyl)alkyl, hydroxy, alkoxy, aryloxy, acyl, ester mercapto, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino and di-substituted amino, wherein each Ar group is independently substituted with at least one halogen atom.

7. The monomer of claim 6, wherein each Ar group is substituted with two iodine atoms.

8. The monomer of claim 1, wherein R$_1$ at each occurrence is C$_1$-C$_{10}$ alkylene.

9. The monomer of claim 8, wherein R$_1$ is C$_2$-alkylene.

10. The monomer of claim 1, wherein f=1 and both R$_1$ groups further comprise pendant carboxylate ester groups.

11. The monomer of claim 1, wherein B is a methylene group or a methyl-substituted methylene group.

12. The monomer of claim 1, wherein the segment —X$_7$—B—X$_8$— is obtained from a hydroxyl endcapped macromer block comprising at least one macromer block selected from the group consisting of hydroxyl endcapped polycaprolactones, hydroxyl endcapped polylactic acids, hydroxyl endcapped polyglycolic acids, hydroxyl endcapped poly(lactic acid-co-glycolic acids), hydroxyl endcapped poly(alkylene diols), poly(alkylene oxides), and hydroxyl endcapped polydioxanones.

13. The monomer of claim 12, wherein the hydroxyl endcapped macromer block comprises hexane diol.

14. The monomer of claim 12, wherein the hydroxyl endcapped macromer block is a homopolymer.

15. The monomer compound of claim 1, wherein Ar at each occurrence is phenylene, optionally substituted with from one to four substituents per Ar group independently selected from the group consisting of halogen, halomethyl, halomethoxy, methyl, thiomethyl, nitro, sulfoxide and sulfonyl.

16. A monomer compound having the structure of formula:

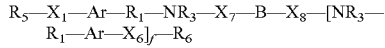

wherein f is 0 or 1;

X$_1$ and X$_6$ are independently selected from the group consisting of O, S and NR$_3$, wherein R$_3$ is selected from the group consisting of hydrogen and alkyl groups containing from one to six carbon atoms;

X$_7$ and X$_8$ are independently selected from the group consisting of —(C=O)—O—, —(C=O)—S—, and —(C=O)—;

wherein Ar at each occurrence is independently selected from the group consisting of phenylene,

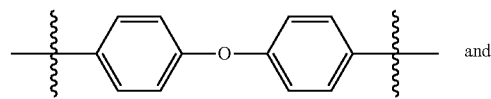

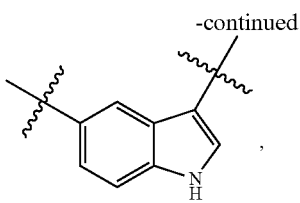

wherein each Ar group is independently substituted with at least one halogen atom, and is optionally further substituted with from one to three substituents per Ar group independently selected from the group consisting of halogen, halomethyl, halomethoxy, methyl, thiomethyl, nitro, sulfoxide and sulfonyl;

wherein $R_1$ at each occurrence is independently selected from the group consisting of optionally substituted $C_1$-$C_{10}$ alkylene, $C_1$-$C_{10}$ heteroalkylene, $C_2$-$C_{10}$ alkenylene and $C_2$-$C_{10}$ heteroalkenylene, wherein at least one occurrence of $R_1$ further comprises a pendant carboxylate ester group containing 2 carbon atoms in addition to the number of carbon atoms defined for said $R_1$ group;

$R_3$ is hydrogen;

$R_5$ and $R_6$ are independently selected from the group consisting of hydrogen and alkyl groups containing from one to six carbon atoms; and B is selected from the group consisting of optionally substituted alkylene groups, optionally substituted heteroalkylene groups, optionally substituted alkenylene groups and optionally substituted heteroalkenylene groups, or B is selected so that the segment —$X_7$—B—$X_8$— is obtained from a starting material $HX_7$—B—$X_8H$, which is selected from a hydroxyl endcapped macromer or a thiol endcapped macromer, wherein the optional substituents on B are selected from the group consisting of alkyl, alkenyl, cycloalkyl, cycloalkenyl, aryl, heteroaryl, heteroalicyclyl, aralkyl, heteroaralkyl, (heteroalicyclyl)alkyl, hydroxy, alkoxy, aryloxy, mercapto, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino and di-substituted amino.

17. The monomer of claim 16, wherein each Ar group is substituted with two iodine atoms.

18. The monomer of claim 1, wherein B is unsubstituted alkylene.

19. The monomer of claim 16, wherein B is unsubstituted alkylene.

* * * * *